United States Patent (10) Patent No.: US 9,784,740 B2
Burford et al.                               (45) Date of Patent:   Oct. 10, 2017

(54) POSITIVE ALLOSTERIC MODULATORS AND SILENT ALLOSTERIC MODULATORS OF THE MU OPIOID RECEPTOR

(71) Applicant: BRISTOL-MYERS SQUIBB COMPANY, Princeton, NJ (US)

(72) Inventors: Neil Burford, Durham, CT (US); Andrew Alt, Durham, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 14/758,908

(22) PCT Filed: Dec. 20, 2013

(86) PCT No.: PCT/US2013/077018
§ 371 (c)(1),
(2) Date: Jul. 1, 2015

(87) PCT Pub. No.: WO2014/107344
PCT Pub. Date: Jul. 10, 2014

(65) Prior Publication Data
US 2015/0338404 A1   Nov. 26, 2015

Related U.S. Application Data

(60) Provisional application No. 61/748,946, filed on Jan. 4, 2013.

(51) Int. Cl.
G01N 33/566 (2006.01)

(52) U.S. Cl.
CPC ...... *G01N 33/566* (2013.01); *G01N 2333/705* (2013.01); *G01N 2333/726* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 7,968,594 B2 | 6/2011 | Guy et al. | |
| 8,846,889 B2 | 9/2014 | Wolfe et al. | |
| 2003/0199424 A1 | 10/2003 | Smith et al. | |
| 2006/0247304 A1* | 11/2006 | Guy | A61K 31/05 514/454 |
| 2010/0130725 A1 | 5/2010 | Fang et al. | |
| 2010/0316678 A1 | 12/2010 | Goodchild | |
| 2011/0112175 A1* | 5/2011 | Wolfe | A61K 48/005 514/44 R |

OTHER PUBLICATIONS

Burford 2011 "strategies for the identification of allosteric modulators of G-protein-coupled receptors" Biochem pharma 81:691-702.*

(Continued)

*Primary Examiner* — Adam M Weidner
(74) *Attorney, Agent, or Firm* — Warren K. Volles

(57) ABSTRACT

Disclosed are positive allosteric modulators (PAMs) and silent allosteric modulators (SAMs) for mu ($\mu$)-opioid receptors that may be useful for the treatment of pain, either alone or in combination with orthosteric opioid receptor agonists. Methods for treating pain and modulating mu ($\mu$)-opioid receptors are also disclosed.

4 Claims, 15 Drawing Sheets

(56) References Cited

OTHER PUBLICATIONS

Burford 2013 "discovery of positive allosteric modulators and silent allosteric modulators of the .mu.-opioid receptor" PNAS 110(26):10830-10835.*

Kathmann 2006 "cannabidiol is an allosteric modulator at mu- and delta-opioid receptors" Nau-Sch Arch Pharmacol 372:354-361.*

Alt, A. et al., "Stimulation of guanosine—5'—O—(3—[$^{35}$S]thio)triphosphate binding by endogenous opioids acting at a cloned Mureceptor," The Journal of Pharmacology and Experimental Therapeutics, 286, pp. 282-288 (1998).

Bassoni, D.L. et al., "Measurements of beta-arrestin recruitment to activated seven transmembrane receptors using enzyme complementation," Methods in Molecular Biology, Clifton, N.J., vol. 897, pp. 181-203 (2012).

Birdsall, N.J. et al., "Allosterism at muscarinic receptors: ligands and mechanisms," Mini Reviews in Medicinal Chemistry, 5, pp. 523-543 (2005).

Bradford, M.M. "A rapid and sensitive method for the quantitation of microgram quantities of protein utilizing the principle of protein-dye binding," Analytical Biochemistry, 72, pp. 248-254 (1976).

Bruns, R.F. et al., "Allosteric enhancement of adenosine A1 receptor binding and function by 2—amino—3—benzoylthiophenes," Molecular Pharmacology, 38, pp. 939-949 (1990).

Burford, N.T. et al., "Discovery of positive allosteric modulators and silent allosteric modulators of the mu—opiod receptor,"Proceedings of the National Academy of Science, vol. 110, No. 26, pp. 10830-10835 (2013).

Burford, N.T. et al., "Strategies for the identification of allosteric modulators of G-protein-coupled receptors," Biochemical Pharmacology, 81, pp. 691-702 (2011).

Clark, M.J. et al, "Comparison of the relative efficacy and potency of μ-opioid agonists to activate $G\alpha_{i/o}$proteins containing a pertussis toxin-insensitive mutation," The Journal of Pharmacology and Experimental Therapeutics, 317, pp. 858-864 (2006).

Clark, M.J. et al., "Endogenous RGS protein action modulates mu-opioid signaling through Galphao. Effects on adenylyl cyclase, extracellular signal-regulated kinases, and intracellular calcium pathways," The Journal of Biological Chemistry, vol. 278, No. 11, 9418-9425 (2003).

Conn, P.J. et al, "Subtype-selective allosteric modulators of muscarinic receptors for the treatment of CNS disorders," Trends in Pharmacological Sciences, vol. 30, No. 3, pp. 148-155 (2009).

Davis, C.N. et al., "Differential regulation of muscarinic M1 receptors by orthosteric and allosteric ligands," BMC Pharmacology, 9, 14 (2009).

Davis, M.P., "Evidence from basic research for opioid combinations," Expert Opinion Drug Discovery, 7(2), pp. 165-178 (2012).

Dietis, N. et al., "Simultaneous targeting of multiple opioid receptors: a strategy to improve side-effect profile,"British Journal of Anaesthesia, 103 (1), pp. 38-49 (2009).

Emmerson, P.J. et al., "Characterization of opioid agonist efficacy in a C6 glioma cell line expressing the mu opioid receptor," The Journal of Pharmacology and Experimental Therapeutics, vol. 278, No. 3, pp. 1121-1127 (1996).

Gao, Z.G. et al., "Allosteric modulation of the adenosine family of receptors," Mini Reviews in Medicinal Chemistry, 5, pp. 545-553 (2005).

Gasparini, F. et al., "Allosteric modulators of group I metabotropic glutamate receptors: novel subtype-selective ligands and therapeutic perspectives," Current Opinion in Pharmacology, 2, pp. 43-49 (2002).

Gjoni, T. et al., "Receptor activation involving positive allosteric modulation, unlike full agonism, does not result in $GABA_B$receptor desensitization," Neuropharmacology, 55, pp. 1293-1299 (2008).

Jacoby, E. et al., "The 7T G-Protein-Coupled Receptor Target Family," ChemMedChem, 1, pp. 760-782 (2006).

Kathmann, M. et al., "Cannabidiol is an allosteric modulator at mu- and delta-opiod receptors,"Naunyn-Schmiedeberg's Archives of Pharmacology, 372, pp. 354-361 (2006).

Kenakin, T.P., "'7TM receptor allostery: putting numbers to shapeshifting proteins," Trends in Pharmacological Science, vol. 30, No. 9, pp. 460-469 (2009).

Koole, C. et al, "Allosteric ligands of the glucagon-like peptide 1 receptor (GLP-1R) differentially modulate endogenous and exogenous peptide responses in a pathway-selective manner: implications for drug screening," Molecular Pharmacology, 78, pp. 456-465 (2010).

Langmead, C.J., "Ligand properties and behaviours in an allosteric age," Trends in Pharmacological Sciences, vol. 33, pp. 621-622 (2012).

Lee, K.O. et al, "Differential binding properties of oripavines at cloned mu- and delta-opioid receptors," European Journal of Pharmacology, 378, pp. 323-330 (1999).

Lester, P.A. et al., "Comparison of the in vitro efficacy of mu, delta, kappa and $ORL_1$ receptor agonists and non-selective opioid agonists in dog brain membranes," Brain Research, 1073-1074, pp. 290-296 (2006).

Levine, J.D. et al., "The narcotic antagonist naloxone enhances clinical pain," Nature, vol. 272, pp. 826-827 (1978).

Manglik, A. et al., "Crystal structure of the μ-opioid receptor bound to a morphinan antagonist," Nature, vol. 485, pp. 321-326 (2012).

Matthes, H.W.D. et al., "Loss of morphine-induced analgesia, reward effect and withdrawal symptoms in mice lacking the μ-opioid-receptor gene," Nature, vol. 383, pp. 819-823 (1996).

McNicol, E. et al., "Management of opioid side effects in cancer-related and chronic noncancer pain: a systematic review," The Journal of Pain, vol. 4, No. 5, pp. 231-256, (2003).

Neilan, C.L. et al, "Constitutive activity of the delta-opioid receptor expressed in C6 glioma cells: identification of non-peptide delta-inverse agonists," British Journal of Pharmacology, 128, pp. 556-562 (1999).

Noetzel, M. J. et al, "Functional impact of allosteric agonist activity of selective positive allosteric modulators of metabotropic glutamate receptor subtype 5 in regulating central nervous system function," Molecular Pharmacology, 81, pp. 120-133 (2012).

Overington, J.P. et al., "How many drug targets are there?" Nature Reviews, vol. 5, pp. 993-996 (2006).

Peng, D. et al., "Recent Progress in Study of Opioid Receptors," Medical Recapitulate, vol. 21, No. 24, pp. 4444-4447 (2015) [English abstract only].

Roques, B.P. et al., "Inhibiting the breakdown of endogenous opioids and cannabinoids to alleviate pain," Nature Reviews, vol. 11, pp. 292-310 (2012).

Rothman R.B. et al., "Salvinorin A: Allosteric Interactions at the mu-Opioid Receptor," Journal of Pharmacology and Experimental Therapeutics, vol. 320, No. 2, pp. 801-810 (2006).

Schann, S. et al., "Chemical Switch of a Metabotropic Glutamade Receptor 2 SIlent Allosteric modulator into Dual Metabotropic Glutamate Reeptor 2/3 Negative/Positive Allosteric Modulators," Journal of Medicinal Chemistry, vol. 23, No. 24, pp. 8775-8779 (2010).

Sharma, S. et al, "Synthesis and SAR of a mGluR5 allosteric partial antagonist lead: Unexpected modulation of pharmacology with slight structural modifications to a 5-(phenylethynyl)pyrimidine scaffold," Bioorganic & Medicinal Chemistry Letters, 18, pp. 4098-4101 (2008).

Shukla, A.K. et al., "Emerging paradigms of beta-arrestin-dependent seven transmembrane receptor signaling," Trends in Biochemical Sciences, vol. 36, No. 9, pp. 457-469 (2011).

Waldhoer, M. et al., "Opioid Receptors," Annual Review of Biochemistry, 73, pp. 953-990 (2004).

Whalen, E.J. et al., "Therapeutic potential of β-arrestin- and G protein-biased agonists," Trends in Molecular Medicine, vol. 17, No. 3, pp. 126-139 (2011).

* cited by examiner

POSITIVE ALLOSTERIC MODULATORS AND SILENT ALLOSTERIC MODULATORS OF THE MU OPIOID RECEPTOR

CROSS REFERENCE TO RELATED APPLICATION

This application claims the priority of U.S. Provisional Application Ser. No. 61/748,946 filed Jan. 4, 2013 which is herein incorporated by reference.

DESCRIPTION OF THE INVENTION

A Bibliography is appended hereto that contains references (1) through (34), each of which is incorporated by reference herein.

The invention is specifically described herein with respect to two compounds, i.e., BMS-986121 and BMS-986122 (shown in FIG. 1), which are presented for purposes of exemplification.

The application of the invention is not intended to be limited in scope to these two compounds. Instead, the application of the invention is intended to cover any compounds which function to provide the desirable aspects of the invention. In particular, compounds to which the invention may be applicable include any compounds which function to bind to the opioid receptors and enhance the binding affinity or efficacy (or both) of an orthosteric agonist.

The superfamily of G protein-coupled receptors (GPCRs), comprises plasma membrane spanning proteins that transduce signals via heterotrimeric G proteins on the inner surface of the plasma membrane leading to intracellular signaling cascades involved in many aspects of cellular function (1). The cell surface location, tissue distribution, and diversity of these GPCRs make them ideal targets for drug intervention. Indeed, about 30% of marketed drugs target specific GPCR activity (1, 2).

Opioid receptors are members of the Class A family of GPCRs. Four opioid receptor types exist (mu, delta, kappa, and ORL1) which share about 60% amino acid identity (mainly in the transmembrane domains) and signal through the Gi/o family of heterotrimeric G proteins, resulting in inhibition of adenylyl cyclase, modulation of ion channel activity, and transcriptional changes in the cell (3). Opioid receptors (and many other GPCRs) can also signal through non-G-protein mediated pathways, one of which is initiated by β-arrestin recruitment to the receptor. β-arrestin is involved in receptor desensitization and internalization/recycling (4, 5). Opioid receptors are key targets in the management of pain and morphine and its derivatives induce pain relief by acting as agonists at opioid receptors, especially the mu-opioid receptor (6, 7). Opioid receptors have been extensively studied because of the need for better pain control while trying to reduce or eliminate adverse side effects. These side effects include tolerance, respiratory suppression, constipation, allodynia, and dependence (3, 8).

To overcome these side effects, studies have focused on developing more selective agonists, which target one specific opioid receptor type over the others, or partial agonists (which have reduced efficacy compared to full agonists), or agonists used together in combination therapy (9, 10). However, these diverse approaches have a single commonality in that they target the orthosteric (endogenous) agonist binding site of the receptor. A different approach that has been used successfully with other GPCRs is the discovery and development of allosteric ligands, which can have specific advantages over their orthosteric counterparts.

Allosteric ligands for a GPCR bind to a site on the receptor that is distinct from the site that binds the orthosteric (or endogenous) agonist (11, 12). An allosteric modulator (AM) can exhibit a range of activities at the target protein. Positive allosteric modulators (PAMs) may have no intrinsic efficacy, but when they bind to the receptor enhance the binding affinity or efficacy (or both) of the orthosteric agonist. Negative allosteric modulators (NAMs) have no intrinsic efficacy, but when they bind to the receptor inhibit the binding affinity or efficacy (or both) of the orthosteric agonist. Silent allosteric modulators (SAMs), also known as neutral allosteric ligands (NALs), bind to the receptor but have no effect on orthosteric agonist affinity or efficacy. However, SAMs can act as competitive antagonists at the same allosteric site, blocking PAM or NAM activity. Although not particularly useful from a therapeutic standpoint, SAMs can be effective tools to show that presumed PAM or NAM effects are receptor mediated. Finally, allosteric agonists can bind and produce direct agonist activation of the receptor even in the absence of orthosteric agonist.

Allosteric ligands have the potential to exhibit greater selectivity between subtypes of GPCRs in the same family compared with orthosteric ligands. This has been demonstrated for some GPCRs including metabotropic glutamate receptors, adenosine receptors and muscarinic receptors (13-17). This increased selectivity is hypothesized to be based on the evolutionary constraint placed on the orthosteric site between closely related receptor subtypes that bind the same endogenous ligand. This evolutionary constraint may not be required for allosteric sites.

While highly selective orthosteric agonist ligands exist for opioid receptors, additional advantages of PAMs provide intriguing opportunities for opioid receptor PAMs as potential therapeutics in pain management.

PAMs, unlike allosteric agonists, may have no effect when they bind to the receptor in the absence of orthosteric agonist. Therefore, the modulation occurs only when an orthosteric agonist is bound to the receptor. In vivo, this leads to preservation of the temporal and spatial characteristics of cell signaling; this is important, especially for signaling in the complex neuronal networks in the brain and enteric nervous system. Additionally, by preserving the temporal aspects of native receptor signaling, PAMs may avoid receptor down-regulation and other compensatory mechanisms that are triggered by sustained receptor activation produced by exogenous orthosteric agonists. Therefore, opioid receptor PAMs could be expected to produce less tolerance and dependence than exogenous orthosteric agonists. Here, we describe the discovery and characterization of mu-opioid receptor PAMs and SAMs. A high-throughput screen (HTS) was developed and executed using a β-arrestin recruitment assay. Mu-selective PAMs resulting from the HTS were shown to be active in both β-arrestin recruitment assays, and in G-protein mediated signaling assays (inhibition of adenylyl cyclase activity and [$^{35}$S]GTPγS binding). These studies are the first to describe the existence of mu-selective PAMs and SAMs implicating positive allostery as a potential novel avenue for the discovery of tightly regulated pain therapeutics.

Potential opioid receptor ligands were identified from an HTS campaign using the PathHunter® enzyme complementation assay technology (DiscoveRx, CA) (18). In this system an N-terminal deletion mutant of β-galactosidase, termed enzyme acceptor (EA), is fused to the C-terminus of stably expressed β-arrestin 2 in U2OS cells. A mutated amino-terminal fragment of β-galactosidase, termed Pro-Link™ (PK), is fused to the carboxyl terminus of the OPRM1 receptor recombinantly expressed in these cells (U2OS-OPRM1). Binding of arrestin to the activated mu-opioid receptor results in a complementation of the enzyme and reconstitution of enzyme activity. Thus, complemented enzyme activity can be used as a measure of the recruitment of arrestin to the mu-opioid receptor. The HTS campaign was performed in the presence of a low (20 nM, ~$EC_{10}$) concentration of the mu-selective orthosteric agonist, endomorphin-I, to identify both agonists and positive allosteric modulators (PAMs). Two compounds were identified as potential mu-opioid receptor PAMs (mu-PAMs). These compounds have been designated as BMS-986121 and BMS-986122, and their structures are shown in FIGS. 1A and B. Neither BMS-986121 nor BMS-986122 produced significant β-arrestin recruitment on their own (agonist detection mode), but both compounds significantly augmented the β-arrestin recruitment response produced by a low concentration of endomorphin-I (PAM detection mode) (FIGS. 1C and D). In PAM detection mode, BMS-986121 increased β-arrestin recruitment by 20 nM endomorphin-I to $E_{max}$ (95% CI) of 72 (66-78) % of the response evoked by a maximally effective (1 uM) concentration of endomorphin-I, with an $EC_{50}$ (95% CI) of 1.0 (0.7-1.4) uM. BMS-986122 produced a similar PAM detection mode response increasing the effect of the low concentration of endomorphin-I to 79 (73-84) % of the maximal endomorphin-I response with an $EC_{50}$ of 3.0 (2.3-3.8) uM.

To test the specificity of the response, the compounds were examined in a similar assay in U2OS PathHunter® cells expressing PK-tagged delta opioid receptors (U2OS-OPRD1). Neither compound had any significant effect in the absence (agonist detection mode) or the presence (PAM detection mode) of a ~$EC_{10}$ (0.4 nM) of the delta agonist leu-enkephalin (FIGS. 1C and D). These results suggest that the effects of BMS-986121 and BMS-986122 are mediated through activation of mu-opioid receptors and that the compounds are selective for mu-over delta-opioid receptors.

To further assess mu-PAM activity BMS-986121 and BMS-986122 were tested in three functional assays, β-arrestin recruitment, inhibition of adenylyl cyclase activity, and G protein activation using [$^{35}$S]GTPγS binding. Compounds were also assessed in receptor binding assays.

Concentration-response curves (CRCs) for endomorphin-I-mediated recruitment of β-arrestin were generated in the absence or presence of varying concentrations of each mu-PAM. BMS-986121 (FIG. 2A) or BMS-986122 (FIG. 2B) produced concentration-dependent and saturable leftward shifts in the potency of endomorphin-I. BMS-986121 produced a maximal 9-fold increase in the potency of endomorphin-I. The concentration of BMS-986121 that produced a half-maximal leftward shift was 1.7 uM. BMS-986122 produced a maximal 8-fold increase in the potency of endomorphin-I, with a half maximal leftward shift value of 4.9 uM (FIG. 2C).

Opioid receptors inhibit adenylyl cyclase via $G\alpha_{i/o}$ proteins (19). In order to assess the effects of the mu-PAMs on this signaling pathway, their effects were measured in a cAMP accumulation assay. The cAMP inhibition responses produced by opioid agonists in the U2OS PathHunter® cells were small and inadequate for robust measurement. Therefore, a Chinese hamster ovary (CHO) cell line recombinantly expressing human mu opioid receptors (CHO-mu) was used for these experiments. In this cell line, mu-opioid receptor agonists produce robust and reproducible inhibition of forskolin (1 uM)-stimulated cAMP accumulation. Endomorphin-I produced a 17-fold reduction in cAMP accumulation with an $EC_{50}$ of 76 (60-96) pM (FIG. 6). BMS-986121 and BMS-986122 significantly increased the inhibition of forskolin-stimulated adenylyl cyclase activity produced by a ~$EC_{10}$ (30 pM) concentration of endomorphin-I in CHO-mu cells (FIGS. 3A and B). BMS-986121 and BMS-986122 both afforded potentiation with $EC_{50}$ values of 2.2 (1.7-2.8) and 8.9 (6.1-13.1) uM respectively. The maximal inhibition produced by endomorphin-I in the presence of the PAMs was similar to that of a maximal concentration (10 nM) of endomorphin-I alone. In this assay both mu-PAMs also exhibited some intrinsic agonist activity causing inhibition of cAMP accumulation in the absence of any orthosteric agonist (FIG. 3, Compounds A and B). The low efficacy agonist activity of BMS-986121 ($EC_{50}$ of 14 (2-100) uM; $E_{max}$ of 35 (6-63) %) was not always reproducible and on some occasions, was too low to determine a fit of the concentration response data. BMS-986122 agonist activity ($EC_{50}$ of 41 (20-86) uM; $E_{max}$ of 60 (24-95) %) was more apparent. The agonist activity of BMS-986121 and BMS-986122 was only seen at concentrations above those required to produce significant potentiation of an endomorphin-I response, and both agonist responses failed to reach the maximal effect of endomorphin-I.

The discrepancy between the agonist activity of the PAMs seen in this assay and the lack of agonist activity seen in the β-arrestin recruitment assay in U2OS-OPRM1 cells may be due to differences in apparent receptor reserve for the two assays and/or cell-lines. In the recombinant CHO cells, endomorphin-I is ~1000-fold more potent for inhibition of forskolin-stimulated cAMP accumulation in comparison with arrestin recruitment in U2OS PathHunter® cells, suggesting that significant levels of receptor reserve are present in the cAMP assay compared with the arrestin assay. It has been shown previously that PAMs can exhibit agonist activity (albeit at higher concentrations than those seen for PAM activity) in recombinant cells expressing high levels of GPCR protein (20). Indeed, it has been suggested that PAMs are aspiring allosteric agonists, and the degree of agonist efficacy observed depends largely on the sensitivity of the system and assay used to detect signals (21).

Next, the mu-PAMs were characterized in G protein activation [$^{35}$S]GTPγS binding studies in membranes from C6 glioma cells stably expressing recombinant mu-opioid receptors (C6mu) (22). Agonist-stimulated [$^{35}$S]GTPγS binding was determined after a 5 min. incubation to capture the initial rate of G protein activation which can differentiate partial agonists from full agonists in this cell line. The mu-opioid receptor agonist DAMGO at 10 uM produced a 250% stimulation of [$^{35}$S]GTPγS binding above basal activity, with an $EC_{50}$ of 222 (179-274) nM. BMS-986121 (10 uM) resulted in a 4-fold leftward shift in the DAMGO CRC ($EC_{50}$ of 57 (37-89) nM) (FIG. 4A). BMS-986122 (10 uM) resulted in the DAMGO CRC shifting leftwards by 7-fold ($EC_{50}$ of 32 (25-40) nM) (FIG. 4B). No significant agonist activity was detected for either of the PAM compounds in this assay.

Mu-opioid receptor ligand binding was determined in the presence of 100 mM NaCl and 10 uM GTPγS. In saturation binding studies the mu-PAM, BMS-986122, did not affect [$^3$H]diprenorphine binding affinity ($K_d$ in the presence of vehicle was 0.27 (0.21-0.32) nM; $K_d$ in the presence of BMS-986122 (10 uM) was 0.35 (0.18-0.51) nM) but significantly increased the affinity of DAMGO by 6-fold in competition studies with 0.2-0.3 nM [$^3$H]diprenorphine binding ($K_i$ in the presence of vehicle was 340 (208-552) nM; $K_i$ in the presence of BMS-986122 (10 uM) was 56 (41-76) nM) (FIG. 4, Compound E; FIG. 7, Compound A; Table S1). These data suggest that BMS-986122 is, at least in part, a positive affinity modulator of the mu-opioid receptor for the orthosteric agonist DAMGO.

Enhancement of the maximal response to a partial agonist in the [$^{35}$S]GTPγS binding assay would suggest that the mu-PAMs are able to modulate observed efficacy in this system. Morphine produced an $E_{max}$ of 42 (38-45) % of the response induced by 30 uM DAMGO after 5 min. incubation with [$^{35}$S]GTPγS, with an $EC_{50}$ of 110 (71-171) nM (FIGS. 4C and D). This confirms that morphine is a partial agonist in this assay system relative to DAMGO (22). BMS-986121 increased morphine potency by 2.5-fold ($EC_{50}$ of 45 (29-68) nM) (FIG. 4C). The potency of morphine was shifted to the left 3-fold in the presence of 10 uM BMS-986122 ($EC_{50}$ 38 (24-61) nM) (FIG. 4D). The maximal effect ($E_{max}$) of morphine compared to DAMGO was increased by BMS-986121 (72 (67-78) %) (FIG. 4C) and by BMS-986122 (74 (68-81) %) (FIG. 4D). These data confirm that BMS-986121 and BMS-986122 can positively modulate the observed efficacy, measured as an increase in maximal response of the partial agonist morphine in this system.

The previous experiments used heterologous cell systems expressing high concentrations of receptors. To determine whether mu-PAM activity can be observed in native tissues, DAMGO-stimulated [$^{35}$S]GTPγS binding in membranes from mouse brain was assessed (FIG. 4F). The potency of DAMGO to stimulate [$^{35}$S]GTPγS binding ($EC_{50}$ of 458 (245-856) nM) was shifted to the left 4.5-fold in the presence of BMS-986122 ($EC_{50}$ of 101 (56-183) nM). No agonist activity was observed with BMS-986122. Therefore, mu PAM activity can also be observed for DAMGO-mediated G protein activation in membranes from a physiologically relevant tissue with endogenous levels of receptor and G-protein.

A number of close analogs of BMS-986122 were tested in the β-arrestin recruitment assay in order to explore the structure-activity relationship (SAR) of the chemical series. Of the 15 analogs tested, 13 showed at least some PAM activity at the mu receptor. None of these compounds showed agonist activity at the mu-opioid receptor (FIG. 8). However, 5 of the analogs did show some low efficacy agonist or PAM activity at the delta receptor (FIG. 8), suggesting that modifications to this chemotype may alter the selectivity for mu-opioid vs. delta-opioid receptors. Modifications to the structure of BMS-986122 affected the compounds' PAM activity in U2OS-OPRM1 cells (FIG. 8; Table S2). For the most part, the analogs examined retain similar potencies relative to BMS-986122 ($EC_{50}$ values in the low μM range). However, minor changes to the structure of BMS-986122 led to a pronounced reduction in the $E_{max}$ values observed in PAM detection mode. This can be inferred to correspond to a decrease in the maximum leftward shift in endomorphin-I potency that can be produced by a compound. Of the analogs tested, none exhibited greater PAM activity than the original screening hit BMS-986122.

It has been observed that allosteric modulators of GPCRs can often exhibit "activity switching" within a chemical series: minor modifications in the chemical structure can change a compound from a PAM to a negative (NAM) or silent (SAM) allosteric modulator (23). The absence of observed PAM efficacy in 2 of the analogs may be due to loss of binding affinity, or functional switching from PAMs to NAMs or SAMs. Therefore, two of these BMS-986122 analogs (designated BMS-986123 and BMS-986124) were assessed for their ability to inhibit orthosteric agonist activity (in a NAM detection mode assay), or for their ability to inhibit BMS-986122 PAM activity (a SAM detection mode assay) in the β-arrestin recruitment assay in U2OS-OPRM1 cells and in the [$^{35}$S]GTPγS assay in C6mu cells. Neither compound significantly inhibited an $EC_{80}$ concentration of endomorphin-I (300 nM) (FIG. 9) suggesting that they are not NAMs or orthosteric antagonists. However, both compounds were able to inhibit the PAM response to 12.5 uM ($~EC_{80}$) BMS-986122 in U2OS-OPRM1 cells in the presence of 30 nM ($~EC_{20}$) endomorphin-I (FIG. 5, Compound A). Calculated $K_b$ values (the inhibition constant for a competitive antagonist which at equilibrium would occupy 50% of the receptors in the absence of agonist) for SAM activity of BMS-986123 and BMS-986124 were 1 uM and 2 uM, respectively (Table S2). In a separate set of experiments, DAMGO potency to stimulate [$^{35}$S]GTPγS binding in C6mu cell membranes ($EC_{50}$ of 224 (167-300) nM) was again enhanced 8-fold in the presence of BMS-986122 (10 uM) ($EC_{50}$ of 29 (22-38) nM) (FIG. 5, Compound B, FIG. 10). Co-addition of BMS-986122 (10 uM) with BMS-986124 (50 uM), resulted in an inhibition of the PAM effect, with DAMGO potency enhanced less than 2-fold ($EC_{50}$ of 128 (97-168) nM) compared to the DAMGO potency in the presence of the vehicle control (FIG. 5, Compound B; FIG. 10). Together these data confirm that the PAM effects of BMS-986122 can be antagonized by BMS-986124 and strongly suggest that BMS-986123 and BMS-986124 are mu-opioid receptor SAMs (mu-SAMs), competitive antagonists at the allosteric site to which BMS-986122 binds.

The mu-SAM, BMS-986123, produced a small (~2-fold) but significant decrease in [$^3$H]diprenorphine binding affinity (FIG. 7) but had no significant effect on DAMGO binding affinity (Table 6). The potency of DAMGO or morphine in the [$^{35}$S]GTPγS assay was not significantly increased by BMS-986123 or BMS-986124 (FIGS. 11 and 12) at 10 uM, although both SAMs increased morphine $E_{max}$ to a small degree (FIG. 12). No significant agonist activity was detected for either of the SAM compounds in this assay.

Probe dependence (the ability of an allosteric modulator to modulate one orthosteric agonist but not another) is a striking characteristic of some allosteric modulators (24). BMS-986121 (100 uM) produced leftward shifts in the potency of endomorphin-I (4.3-fold), morphine (6.5-fold), and leu-enkephalin (4.5-fold), in inhibition of forskolin-stimulated cAMP accumulation assays in CHO-mu cells (FIG. 13). Taken together with the DAMGO and morphine data sets from the [$^{35}$S]GTPγS binding studies and the β-arrestin data, there is no current evidence to suggest strong probe dependence as BMS-986121 produced similar potentiation of peptide agonist- and small molecule agonist-evoked responses.

As noted above, PAMs (unlike allosteric agonists) generally only modulate the activity of the receptor when an orthosteric agonist is bound, maintaining the temporal and spatial aspects of cell signaling in vivo. Therefore, PAMs have a striking advantage over their orthosteric agonist counterparts. With traditional agonist ligands, the receptor is turned on for long periods (based on the dosing regime), often resulting in adverse effects, such as desensitization of the receptor response or receptor-mediated side-effects caused by long-term stimulation. In the case of opioid receptors, long-term dosing with opiates leads to the development of tolerance and dependence, as well as other acute receptor-mediated side-effects such as, respiratory suppression, constipation and allodynia (3, 8). We have determined that the mu-PAMs described here can positively modulate mu-opioid receptor responses to the endogenous agonists endomorphin-I and leu-enkephalin. It will be important to determine whether mu-PAMs can produce antinociceptive effects when administered alone in vivo, potentiating responses to endogenous opioid agonists. Evidence for a basal tone of mu-opioid receptor activation does exist. For example, inhibition of enkephalinases which breakdown endogenous opioid peptides results in antinociception in animal models of inflammatory and neuropathic pain (25). In addition, the opioid receptor antagonist naloxone increased pain perception when administered to post-operative patients who were not taking exogenous opiates, suggesting that endogenous opioid peptides produce a basal analgesic tone, which can be reduced by naloxone (26).

Another advantage of PAMs is their ability to shift the potency of orthosteric agonist to the left by a finite amount. For example, the analogs of BMS-986122 (Table S2) showed a differential ability to shift the potency of orthosteric agonist to the left, resulting in different $E_{max}$ values when the compounds were co-administered with a low dose of endomorphin-I. Drug development programs can take advantage of this finite potency shift to improve safety by designing PAMs that cannot exceed the required level of effect.

Opioid receptor tolerance and dependence results from prolonged exposure to opiates resulting in changes in cell function leading to the requirement for increased doses of agonist to mediate the same analgesic effect. One can predict that a lower dose of morphine administered together with a mu-PAM, might produce the same functional response as a higher dose of morphine alone and so may spare the development of tolerance. It will be important to determine whether the combination of agonist with PAM leads to a reduction in desensitization and/or tolerance and dependence vs. agonist alone. There is some precedence for this with GABA-B receptors. The GABA-B receptor PAM, GS39783, when combined with a low dose of agonist, produced the same level of functional response as a higher dose of GABA-B agonist, yet produced less GABA-B receptor desensitization (27). This may suggest that co-administration of lower doses of opiates with a mu-PAM, may discriminate between the therapeutic analgesic properties of opiates, and their tolerance and dependence liabilities. In addition, there is the possibility that a mu-PAM may bias an orthosteric agonist response away from signaling pathways that mediate tolerance and dependence and other unwanted effects in favor of signaling pathways that mediate a therapeutic response as observed in other systems (24, 27, 28).

In this patent application we have specifically described the discovery and characterization of two mu-opioid receptor-selective PAMs. The BMS-986122 chemotype showed chemical tractability from structure activity relationship studies and also led to the identification of mu-opioid receptor SAMs. To our knowledge these are the first opioid receptor PAMs and SAMs to be described in the literature. The two PAMs show potentiation of orthosteric agonist-mediated β-arrestin recruitment, adenylyl cyclase inhibition, and G protein activation. BMS-986122 potentiates DAMGO-mediated [$^{35}$S]GTPγS binding in mouse brain membranes and appears to be, at least in part, a positive affinity modulator of the mu-opioid receptor for DAMGO binding. These studies provide proof-of-concept for the development of novel opioid allosteric modulators which may have therapeutic potential in chronic pain management with improved side-effects and reduced tolerance and dependence liabilities.

Some of the aspects of the invention are described below.

In one aspect of the invention there is provided a method of screening to identify mu-opioid receptor positive allosteric modulators comprising the steps of:
  (i) adding a positive allosteric modulator test compound and a low concentration of a mu-selective orthosteric agonist to cells either alone or in conjunction with the silent allosteric compound represented by Formula I (BMS-986123);
  (ii) measuring the effect of said mu-selective orthosteric agonist and said test compound on said cells either alone or in the presence of said Formula I compound; and
  (iii) identifying said test compound as being a positive allosteric modulator if said compound of Formula I shows competitive binding with said test compound as evidenced by a decrease in the positive allosteric agonist activity of said test compound.

Preferably, the low concentration of a mu-selective orthosteric agonist is selected from the group consisting of:
  (a) less than or equal to about the calculated EC80 in said cells;
  (b) less than or equal to about the calculated EC70 in said cells;
  (c) less than or equal to about the calculated EC60 in said cells;
  (d) less than or equal to about the calculated EC50 in said cells;
  (e) less than or equal to about the calculated EC40 in said cells;
  (f) less than or equal to about the calculated EC30 in said cells;
  (g) less than or equal to about the calculated EC20 in said cells;
  (h) less than or equal to about the calculated EC10 in said cells.

Preferably, the cells are U2OS cells, CHO cells or C6 glioma cells.

In another aspect of the invention, there is provided a method of screening to identify mu-opioid receptor negative allosteric modulators comprising the steps of:
  (i) adding a negative allosteric modulator test compound and a high concentration of a mu-selective orthosteric agonist to cells either alone or in conjunction with the silent allosteric compound represented by Formula I (BMS-986123);
  (ii) measuring the effect of said mu-selective orthosteric agonist and said test compound on said cells either alone or in the presence of said Formula I compound; and
  (iii) identifying said test compound as being a negative allosteric modulator if said compound of Formula I shows competitive binding with said test compound as evidenced by a decrease in the negative allosteric agonist activity of said test compound.

Preferably, the low concentration of a mu-selective orthosteric agonist is selected from the group consisting of:
  (a) greater than or equal to about the calculated EC10 in said cells;
  (b) greater than or equal to about the calculated EC20 in said cells;
  (c) greater than or equal to about the calculated EC30 in said cells;
  (d) greater than or equal to about the calculated EC40 in said cells;

(e) greater than or equal to about the calculated EC50 in said cells;
(f) greater than or equal to about the calculated EC60 in said cells;
(g) greater than or equal to about the calculated EC70 in said cells;
(h) greater than or equal to about the calculated EC80 in said cells;
(i) greater than or equal to about the calculated EC90 in said cells; and
(j) greater than or equal to about the calculated EC100 in said cells.

Preferably, the cells recombinantly express both an N-terminal deletion mutant of β-galactosidase fused to the C-terminus of β-arrestin 2, in addition to a mutated amino-terminal fragment of β-galactosidase fused to the C-terminus of OPRM1.

Preferably, the mu-selective orthosteric agonist is endomorphin-I.

Preferably, the cells recombinantly express human mu opioid receptor (CHO-mu).

Preferably, the cells recombinantly express human mu opioid receptor (C6-mu).

Preferably, the mu-selective orthosteric agonist is DAMGO.

In another aspect of the invention, there is provided a method to confirm a positive allosteric modulator test compound has mu-opioid receptor positive allosteric modulators comprising the steps of:
(i) adding a positive allosteric modulator test compound and a low concentration of a mu-selective orthosteric agonist to cells either alone or in conjunction with the silent allosteric compound represented by Formula I (BMS-986123);
(ii) measuring the effect of said mu-selective orthosteric agonist and said test compound on said cells either alone or in the presence of said Formula I compound; and
(iii) conforming said test compound has positive allosteric modulating activity if said compound of Formula I shows competitive binding with said test compound as evidenced by a decrease in the positive allosteric agonist activity of said test compound.

Preferably, the low concentration of a mu-selective orthosteric agonist is selected from the group consisting of:
(a) less than or equal to about the calculated EC80 in said cells;
(b) less than or equal to about the calculated EC70 in said cells;
(c) less than or equal to about the calculated EC60 in said cells;
(d) less than or equal to about the calculated EC50 in said cells;
(e) less than or equal to about the calculated EC40 in said cells;
(f) less than or equal to about the calculated EC30 in said cells;
(g) less than or equal to about the calculated EC20 in said cells;
(h) less than or equal to about the calculated EC10 in said cells.

In another aspect of the invention there is provided a method to confirm a negative allosteric modulator test compound has mu-opioid receptor negative allosteric modulators comprising the steps:
(i) adding a negative allosteric modulator test compound and a high concentration of a mu-selective orthosteric agonist to cells either alone or in conjunction with the silent allosteric compound represented by Formula I (BMS-986123);
(ii) measuring the effect of said mu-selective orthosteric agonist and said test compound on said cells either alone or in the presence of said Formula I compound; and
(iii) confirming said test compound has a negative allosteric modulator if said compound of Formula I shows competitive binding with said test compound as evidenced by a decrease in the negative allosteric agonist activity of said test compound.

Preferably, the low concentration of a mu-selective orthosteric agonist is selected from the group consisting of:
(a) greater than or equal to about the calculated EC10 in said cells;
(b) greater than or equal to about the calculated EC20 in said cells;
(c) greater than or equal to about the calculated EC30 in said cells;
(d) greater than or equal to about the calculated EC40 in said cells;
(e) greater than or equal to about the calculated EC50 in said cells;
(f) greater than or equal to about the calculated EC60 in said cells;
(g) greater than or equal to about the calculated EC70 in said cells;
(h) greater than or equal to about the calculated EC80 in said cells;
(i) greater than or equal to about the calculated EC90 in said cells; and
(j) greater than or equal to about the calculated EC100 in said cells.

Preferably, the cells are U2OS cells, CHO cells or C6 glioma cells.

Preferably, the cells recombinantly express both an N-terminal deletion mutant of β-galactosidase fused to the C-terminus of β-arrestin 2, in addition to a mutated amino-terminal fragment of β-galactosidase fused to the C-terminus of OPRM1.

Preferably, the mu-selective orthosteric agonist is endomorphin-I.

Preferably, the cells recombinantly express human mu opioid receptor (CHO-mu).

Preferably, the cells recombinantly express human mu opioid receptor (C6-mu).

Preferably, the mu-selective orthosteric agonist is DAMGO.

In another aspect of the invention, there is provided a method of treating pain in a patient in need thereof comprising administering to the patient a compound which is a positive allosteric modulator for the mu-opioid receptor.

Preferably, the compound is selective for mu-opioid receptors over delta-opioid receptors.

Preferably, the compound is effective to provide augmentation of at least one mu-opioid receptor function selected from G protein activation, inhibition of adenylyl cyclase activity, or b-arrestin recruitment.

In another aspect of the invention, there is provided a method of treating pain in a patient in need thereof comprising administering to the patient a compound which is a positive allosteric modulator for the mu-opioid receptor in combination with another compound which is an orthosteric agonist for the mu-opioid receptor.

Preferably, the compound which is a positive allosteric modulator for the mu-opioid receptor is selective for mu-opioid receptors over delta-opioid receptors Preferably, the compound which is a positive allosteric modulator for the mu-opioid receptor is effective to provide augmentation of at least one mu-opioid receptor function selected from G protein activation, inhibition of adenylyl cyclase activity, or β-arrestin recruitment.

In another aspect of the invention, there is provided a method of modulating the mu-opioid receptor comprising contacting the receptor with a compound that is effective to provide an increase in the receptor function in the presence of orthosteric exogenous or endogenous agonist.

Preferably, the increase in receptor function is observed in maximal effect, potency, or both.

Although the invention has been described with respect to specific aspects, it is intended that the claims made herein shall not be limited to the specific aspects described and that the claims will be entitled to the full scope provided under the law.

Certain of the Materials and Methods used in the experiments described above were as follows.

Reagents and Cells.

PathHunter® β-arrestin U2OS cells engineered to express either Prolink/Enzyme Donor (PK)-tagged OPRM1 (mu-opioid) receptors or Prolink/Enzyme Donor (PK)-tagged OPRD1 (delta opioid) receptors, were from DiscoveRx (Fremont, Calif.). Chinese Hamster Ovary cells (CHO-K1) expressing recombinant mu opioid receptors (CHO-mu) were from PerkinElmer (Waltham, Mass.). C6 glioma cells stably expressing recombinant mu opioid receptors (C6mu) were developed as previously described (29). Cell culture media and supplements were from Life Technologies™ (Carlsbad, Calif.). HTRF® cAMP detection reagents were from Cisbio (Cambridge, Mass.). PathHunter® detection reagents, were from DiscoveRx™ (Fremont, Calif.). Morphine sulfate, leu-enkephalin, β-endorphin, and all other non-opioid ligand biochemical reagents were from Sigma-Aldrich® (St. Louis, Mo.). [$^{35}$S]GTPγS and [$^{3}$H]diprenorphine were from PerkinElmer. All other opioid ligands were from Tocris (Ellisville, Mo.).

β-Arrestin Recruitment Assay

The β-arrestin recruitment assay was performed in U2OS-OPRM1 and U2OS-OPRD1 cell suspensions, according to DiscoveRx established protocols (see SI Methods).

Inhibition of Forskolin-Stimulated cAMP Accumulation Assays.

Inhibition of forskolin-stimulated cAMP accumulation was conducted in CHO-mu cell suspensions using the CisBio HTRF cAMP detection kit with established protocols (see SI Methods).

Cell Membrane Homogenates

C6 glioma cells stably expressing rat MOR (C6mu) were grown and cell membranes were prepared as previously described (30). For mouse brain membranes, mice were euthanized by cervical dislocation. Whole brain tissue, minus cerebellum was removed, immediately chilled in ice-cold 50 mM Tris-HCl, pH 7.4, and membrane homogenates were prepared as described previously (31). Final membrane pellets were resuspended in 50 mM Tris-HCl, pH 7.4, aliquoted and stored at −80° C. Protein content was determined using the method of Bradford (32).

[$^{35}$S]GTPγS Binding Assay

[$^{35}$S]GTPγS binding in membranes was conducted as described previously (22) (see SI Methods).

[$^{3}$H]Diprenorphine Saturation Binding Studies

[$^{3}$H]Diprenorphine saturation binding studies were performed as previously described (33). Briefly, membranes (5 ug) were incubated with 0-4 nM [$^{3}$H]diprenorphine and 10 uM modulator with or without 10 uM naloxone in 100 mM NaCl, 10 uM GTPγS, 5 mM MgCl$_2$ and 50 mM Tris-HCl, pH 7.4 for 80 min. at room temp. Samples were quickly filtered through glass-fiber filter mats as described for [$^{35}$S] GTPγS binding in SI Methods.

[$^{3}$H]Diprenorphine Competition Binding Studies

[$^{3}$H]Diprenorphine competition binding studies were performed as previously described (34). Membranes (10 ug) were incubated with 0.2 nM [$^{3}$H]diprenorphine and 0-10 uM DAMGO with or without 10 uM modulator and/or 10 uM naloxone in 100 mM NaCl, 10 uM GTPγS, 5 mM MgCl$_2$ and 50 mM Tris-HCl, pH 7.4 for 60 min. at room temp. Samples were quickly filtered through glass-fiber filter mats as described for [$^{35}$S]GTPγS binding in SI Methods.

Concentration response data were fit to a logistic equation (eq. 1) using non-linear regression analysis to provide estimates of Ymin (Bottom), Ymax (Top), potency (EC$_{50}$) and slope factor (Hill slope), using GraphPad Prism™ 5.01 (sigmoidal dose response with variable slope).

$$Y = \text{Bottom} + (\text{Top} - \text{Bottom})/(1 + 10^{((\log EC_{50} - X) * \text{HillSlope})}) \quad \text{(eq. 1)}$$

Where P values are described, data were analyzed by 2-way ANOVA with a Bonferroni Post-Test using GraphPad Prism™ 5.01.

β-Arrestin Recruitment Assay

PathHunter® U2OS-OPRM1 and U2OS-OPRD1 cells were grown in modified Eagle medium (MEM) containing 10% fetal bovine serum (FBS), 500 ug/ml G418, and 250 ug/ml hygromycin. Cells were grown to confluence in cell culture Nunc triple-layer flasks (Thermo Fisher Scientific), harvested with TrypLE™ Express, and resuspended in assay buffer (Hanks Buffered Salt Solution (HBSS)+25 mM HEPES, 100 IU/ml penicillin, 100 ug/ml streptomycin, 0.05% BSA at 1×10$^6$ cells/ml. Compounds (20 nl of 100× final concentration in 100% DMSO) were added to white, non-treated 1536-well plates (Corning, N.Y.) by acoustic dispense using an Echo-550 (Labcyte, Sunnyvale, Calif.) from Echo-qualified 1536-well source plates (Labcyte). Next, 1 ul of assay buffer (agonist detection mode), or assay buffer containing a low concentration (~EC$_{10}$) of orthosteric agonist (PAM detection mode), or assay buffer containing a ~EC$_{80}$ concentration of orthosteric agonist (antagonist/NAM detection mode), were added to assay plates. The orthosteric agonists used and their final concentrations are described in the Results. Finally, 1 ul of cells (1000 cells/well) in assay buffer were added to the wells to initiate the incubation period. Plates were lidded and incubated at room temperature for 90 min. Incubations were terminated by the addition of 1 ul PathHunter® Reagent. One hour later luminescence was detected using a Viewlux® imaging plate reader (PerkinElmer). Additional characterization of certain mu-selective PAMs in the β-arrestin assay were performed essentially as described above using the various orthosteric agonist ligands and cell lines described in the Results.

Inhibition of Forskolin-Stimulated cAMP Accumulation Assays.

CHO cells expressing recombinant human mu-opioid receptor (CHO-mu) were grown to confluence in F12 media containing 10% FBS, 100 IU/ml penicillin, 100 ug/ml streptomycin and 400 ug/ml G418 in T-175 tissue culture flasks (Corning) and harvested with TripLE™ Express. Cells were pelleted by centrifugation and resuspended in assay buffer at 6.67×10$^5$ cells/ml.

Compounds (30 nl of 100×final concentration in 100% DMSO) were added to 1536-well white solid non-treated plates by acoustic dispense using an Echo-550. Next, 1.5 ul of assay buffer containing 1 mM IBMX and 2× forskolin (1 uM final), without (agonist detection mode) or with (PAM detection mode) 2× endomorphin-I (30 pM final, a ~$EC_{10}$ concentration) were added to the plates. Finally, cells (1.5 ul/well) were added to begin the incubation. Plates were incubated at room temperature for 30 min. followed by the addition of Cisbio HTRF® dynamic cAMP detection reagent (1.5 ul of D2-labelled cAMP tracer in lysis buffer, followed by 1.5 ul of Eu-cryptate conjugated anti-cAMP antibody in lysis buffer). After a 1 hr. incubation at room temperature, time-resolved fluorescence (TRF) was detected on a Viewlux® or Envision® plate reader (PerkinElmer) with excitation at 337 nm and emission reads at 615 nm and 665 nm. The ratiometric data (665 nm read/615 nm read)* 10,000 was then converted to cAMP (nM) based on a standard curve for cAMP (replacing the cell addition step) run at the same time and under identical conditions to the assay.

Characterization of mu-selective PAMs in the CHO-mu cAMP assay, using curve-shift assays and probe dependence assays, were performed as described above, using orthosteric agonists and modulators described in the Results.

[$^{35}$S]GTPγS Binding Assay

Membranes were diluted with 50 mM Tris-HCl, pH 7.4 and pre-incubated with assay buffer containing GDP (1 volume membrane+2 volumes of 2× assay buffer) for 30 min. at room temp. in a shaking water bath. Then 150 ul membrane/assay buffer mix was added to wells containing 50 ul drugs and [$^{35}$S]GTPγS (final concentrations: 20 mM Tris-HCl, pH 7.4, 100 mM NaCl, 5 mM $MgCl_2$, 0.1 mM dithiothreitol, 30-100 uM GDP, 0.1 nM [$^{35}$S]GTPγS, 0-30 uM DAMGO or morphine, 10 uM modulator or DMSO to achieve 2% DMSO final concentration and either 15 ug membrane protein/well for C6mu cell membranes or 10 ug membrane protein/well for mouse brain membranes). After incubation for an additional 5 min. at room temp. samples were quickly filtered through glass-fiber filter mats using a Brandel cell harvester and rinsed 5 times with ice-cold wash buffer (50 mM Tris-HCl, pH 7.4, 100 mM NaCl, 5 mM $MgCl_2$). Filter mats were dried, scintillation cocktail was added, and radioactivity retained on the filters was counted in a Wallac MicroBeta (Perkin Elmer).

Chemical structure and effect of mu-PAMs on β-arrestin recruitment. Chemical structures for two apparent mu-opioid receptor selective positive allosteric modulators (mu-PAMs), designated as BMS-986121 (A) and BMS-986122 (B), were identified from a high-throughput β-arrestin recruitment screen. BMS-986121 (A) and BMS-986122 (B) were assayed at varying concentrations in agonist detection mode (with compound alone) and in PAM detection mode (compound in the presence of a low concentration (~$EC_{10}$) of orthosteric agonist). For mu-opioid receptor expressing cells (U2OS-OPRM1) endomorphin-I (20 nM) was the orthosteric agonist used, and for delta-opioid receptor expressing cells (U2OS-OPRD1) leu-enkephalin (0.4 nM) was the orthosteric agonist used. Data are represented as mean ±s.e.m. of three experiments. In agonist detection mode, 0 and 100% activity represent basal activity and an $E_{max}$ of endomorphin-I (in U2OS-OPRM1, a 6-fold signal) or leu-enkephalin (in U2OS-OPRD1, a 4-fold signal), respectively. In PAM detection mode, 0% activity is normalized to the low concentration (~$EC_{10}$) of orthosteric agonist (endomorphin-I in U2OS-OPRM1 cells, and leu-enkephalin in U2OS-OPRD1 cells). 100% activity represents the response to an $E_{max}$ concentration of these respective agonists.

FIG. 2

Effect of mu-PAMs BMS-986121 and BMS-986122 on endomorphin-I stimulated β-arrestin recruitment in U2OS-OPRM1 cells. Both BMS-986121 (A) and BMS-986122 (B), produced concentration-dependent leftward shifts in the β-arrestin recruitment response to the agonist endomorphin-I. Calculated $EC_{50}$ values (nM) for endomorphin-I at each concentration of compound are shown in each figure legend. The fold leftward shift in $EC_{50}$ values for endomorphin-I in the presence of increasing concentrations of PAM compound is presented (C). Data are represented as mean+/− s.e.m. of 4 experiments.

FIG. 3

Effect of mu-PAMs on inhibition of forskolin-stimulated cAMP accumulation in CHO-mu cells. Both BMS-986121 (A) and BMS-986122 (B) increased the effect of a low (~$EC_{10}$; 30 pM) concentration of endomorphin-I (PAM detection mode) in a concentration-dependent manner. However, both compounds also showed some agonist activity above basal activity when added alone (agonist detection mode). For agonist detection mode, 0% activity represents vehicle (basal) activity. For PAM detection mode, 0% is normalized to the response to a ~$EC_{10}$ (30 pM) concentration of endomorphin-I. The 100% response represents the response to an Emax. concentration of endomorphin-I (10 nM) in both agonist and PAM detection modes. Data are represented as mean±s.e.m. of three experiments.

FIG. 4

Figure 7:
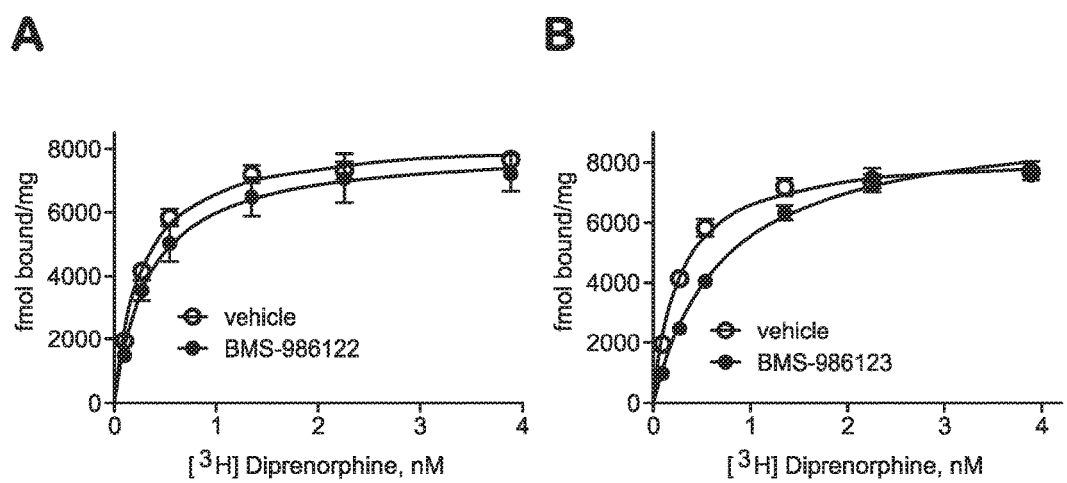

Effect of mu-PAMs on mu-opioid agonist stimulated [$^{35}$S]GTPγS binding in membranes from C6mu cells and mouse brain, and DAMGO binding affinity in C6mu cell membranes. [$^{35}$S]GTPγS binding in C6mu membranes was determined as described in the Methods and Materials. The $EC_{50}$ of DAMGO to stimulate [$^{35}$S]GTPγS binding was shifted to the left 4-fold in the presence of 10 uM of the mu-PAM BMS-986121 (A). BMS-986122 increased the DAMGO potency 7-fold (B). The maximal stimulation by DAMGO was not affected by BMS-986122 or BMS-986121. The mu-PAMs did not significantly affect basal values (vehicle control basal =3.2 ±0.2 fmol bound/mg protein). The $EC_{50}$ of morphine to stimulate [$^{35}$S]GTPγS binding was shifted to the left 2.5-fold in the presence of 10 uM BMS-986121 (C). BMS-986122 (10 uM) increased the morphine potency 3-fold (D). The maximal effect of morphine compared to DAMGO was increased by BMS-986121 (C) and BMS-986122 (D). BMS-986122 (10 uM) produced a 6-fold leftward shift in DAMGO affinity in DAMGO competition binding studies with [$^3$H]diprenorphine (E), but had no effect on [$^3$H]diprenorphine binding affinity (FIG. 7, Table 6). The $EC_{50}$ of DAMGO to stimulate [$^{35}$S]GTPγS binding in membranes from mouse brain was shifted to the left 4.5-fold in the presence of 10 uM BMS-986122 (F). Basal [$^{35}$S]GTPγS binding (4.8±0.4 fmol bound/mg protein) was not affected by 10 uM BMS-986122. Shown are the combined mean ±s.e.m. data from 3-7 separate assays, each performed in duplicate.

FIG. 5

Figure 8:
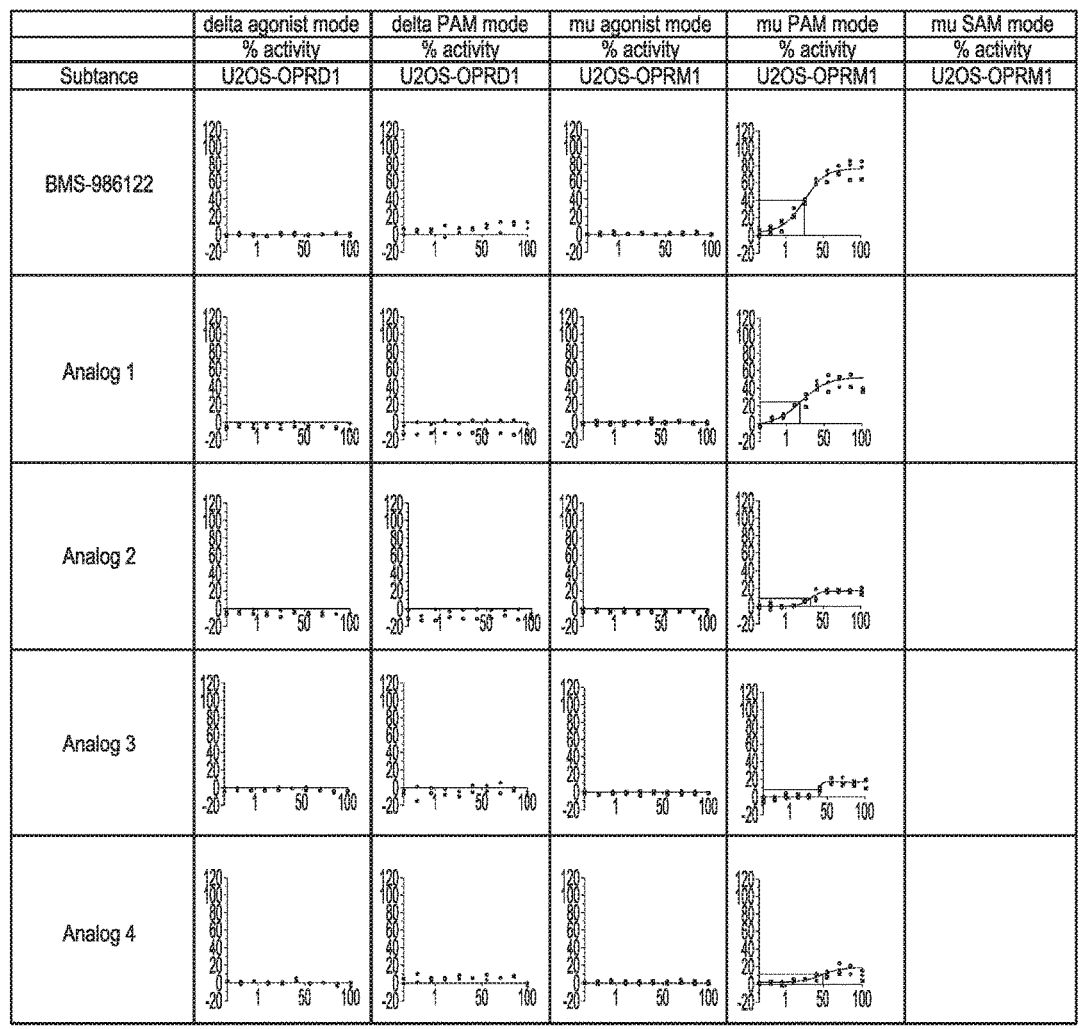
Figure 8:
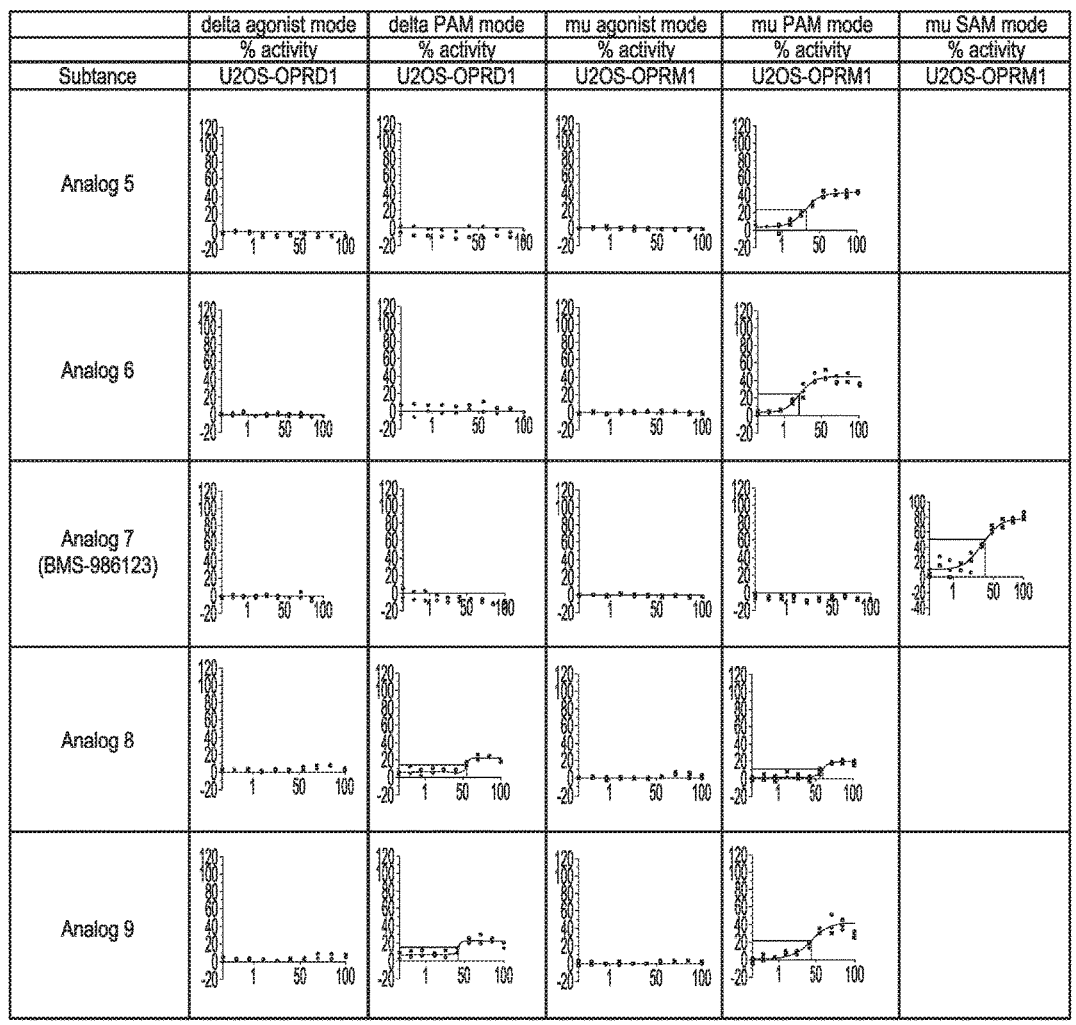
Figure 8:
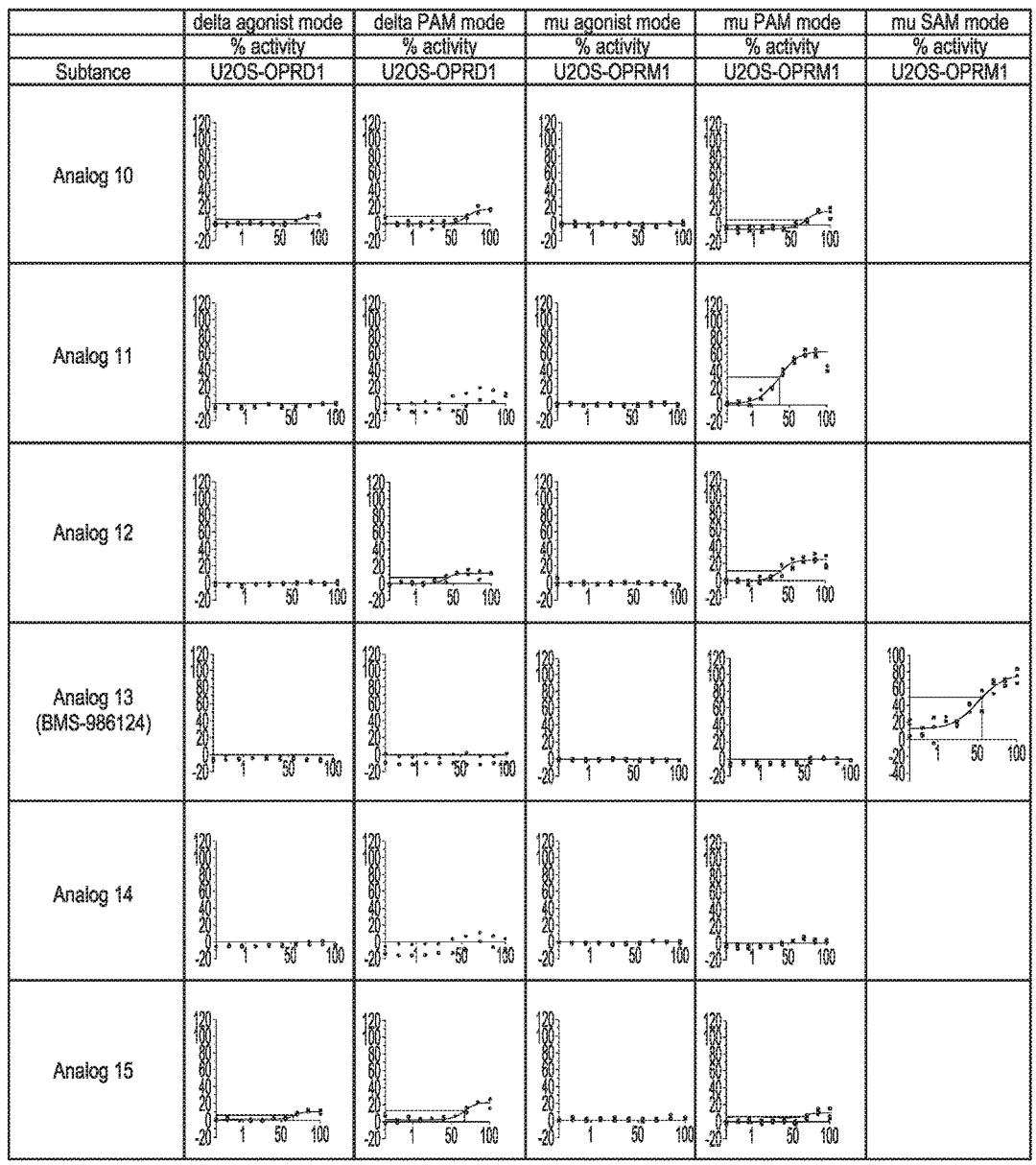
Figure 9:
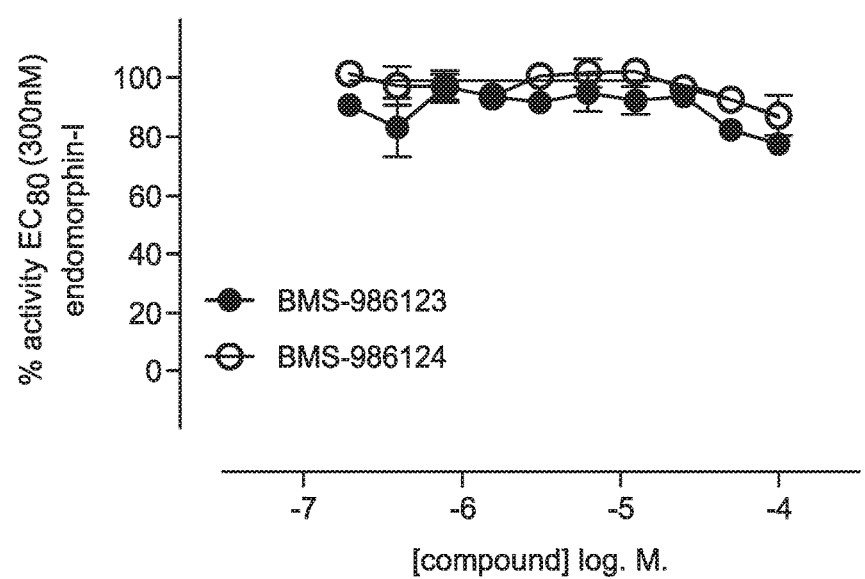
Figure 10:
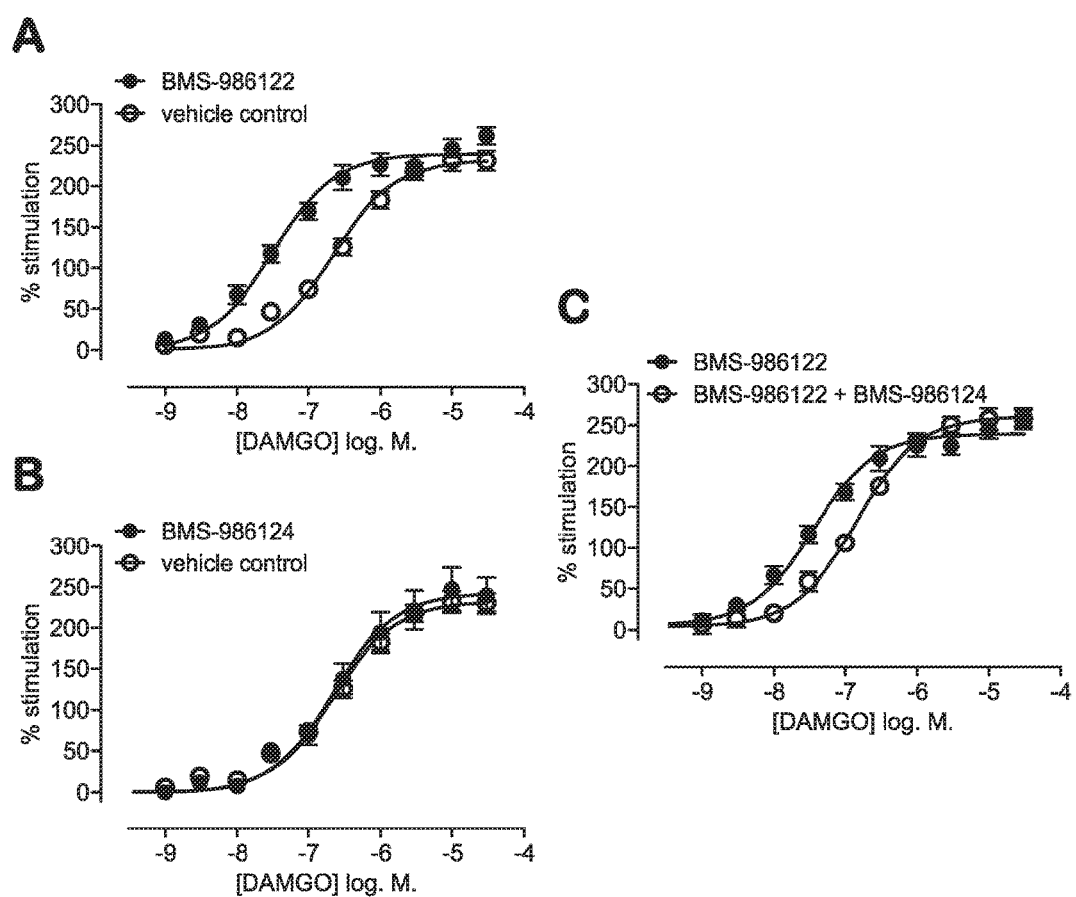
Figure 11:
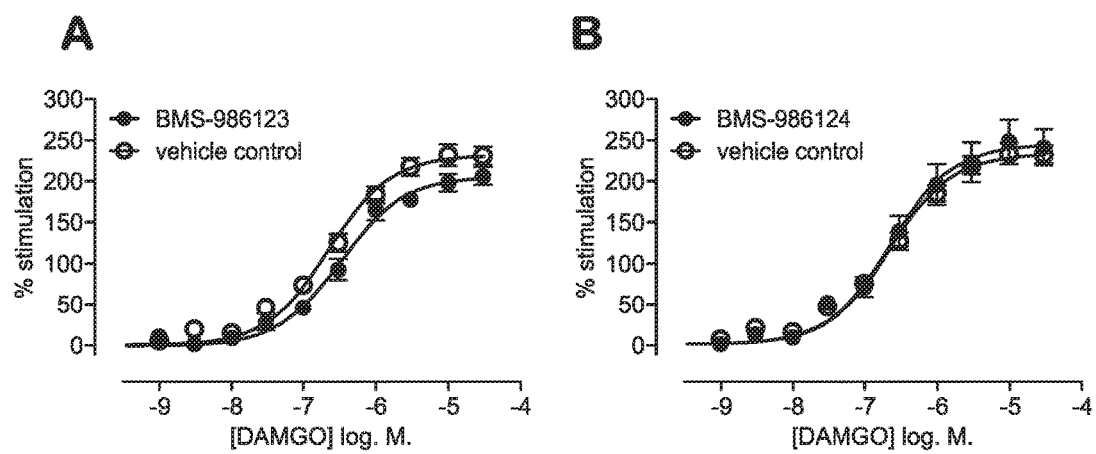
Figure 12:
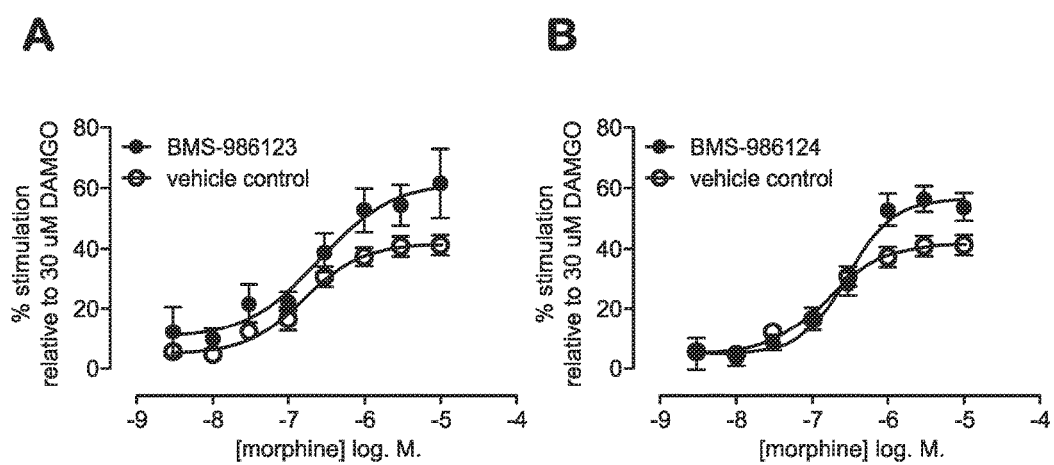
Figure 13:
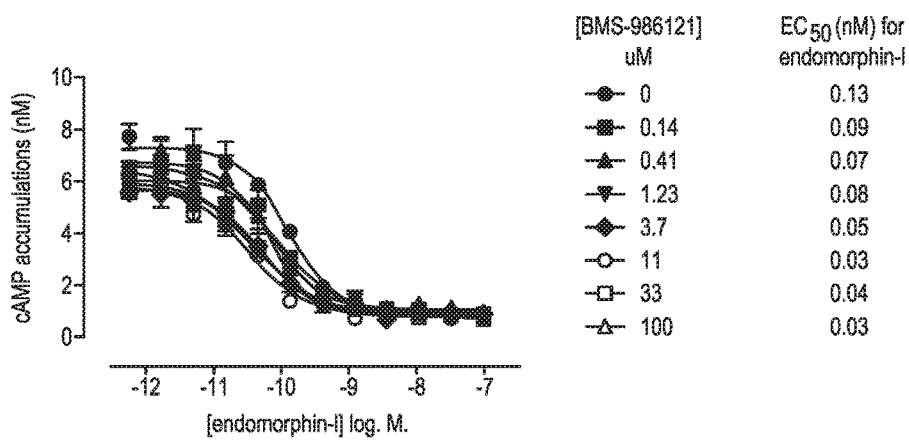
Figure 13:
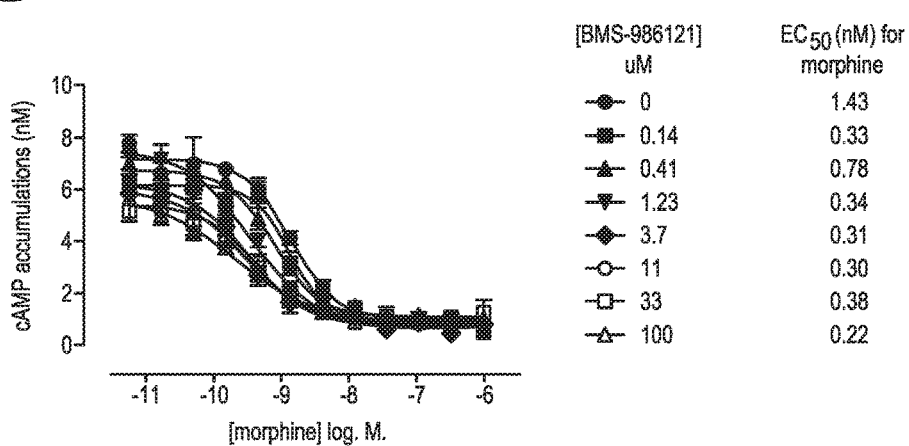
Figure 13:
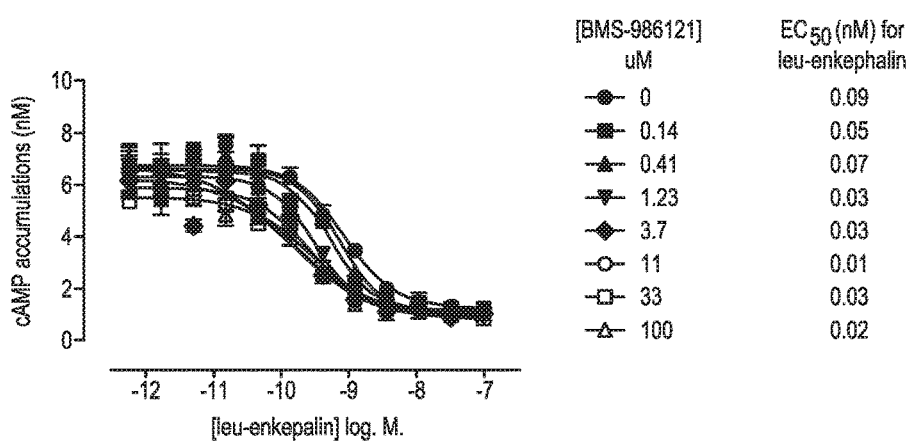

Characterization of functional SAMs in the β-arrestin recruitment assay and in DAMGO-mediated [$^{35}$S]GTPγS binding. (A) BMS-986123 and BMS-986124 inhibited PAM responses to a ~$EC_{80}$ concentration of BMS-986122 (12.5 uM) plus a ˜EC$_{20}$ concentration of endomorphin-I (30 nM) (SAM detection mode) in the β-arrestin recruitment assay in U2OS-OPRM1 cells. 100% activity represents the activity of the combined BMS-986122 plus endomorphin-I, and 0% activity represents the activity of the ˜EC$_{20}$ concentration of endomorphin-I alone. Graphs show the mean ±s.e.m. of three experiments. BMS-986123 and BMS-986124 showed no activity in agonist or PAM detection modes in either U2OS-OPRM1 cells or U2OS-OPRD1 cells (FIG. 8). Similarly, these two compounds showed no NAM/antagonist activity (in the presence of a ˜EC$_{80}$ (300 nM) concentration of endomorphin-I) in U2OS-OPRM1 cells (FIG. 9). (B) DAMGO potency to stimulate [$^{35}$S]GTPγS binding in C6mu membranes was increased 8-fold in the presence of the mu-PAM BMS-986122 (10 uM). Co-incubation of the SAM BMS-986124 (50 uM) with BMS-986122 (10 uM) resulted in only a 2-fold increase in potency for DAMGO suggesting that BMS-986124 can antagonize the BMS-986122 PAM effect. Shown are the combined mean ±s.e.m. data from 3-7 separate assays, each performed in duplicate. EC$_{50}$ values were compared by Student's t-test using GraphPad Prism. (**) represents p<0.01. Concentration response curves for DAMGO-stimulated [$^{35}$S]GTPγS binding under the various conditions are shown in FIG. 10.

FIG. 6

Effect of endomorphin-I on inhibition of 1 uM forskolin-stimulated cAMP accumulation in CHO-mu cells. Endomorphin-I induced a 17-fold reduction in forskolin-stimulated cAMP accumulation with an EC$_{50}$ of 76 (60-96) pM. Data are represented as the mean±s.e.m. of three experiments.

FIG. 7

Figure 1:
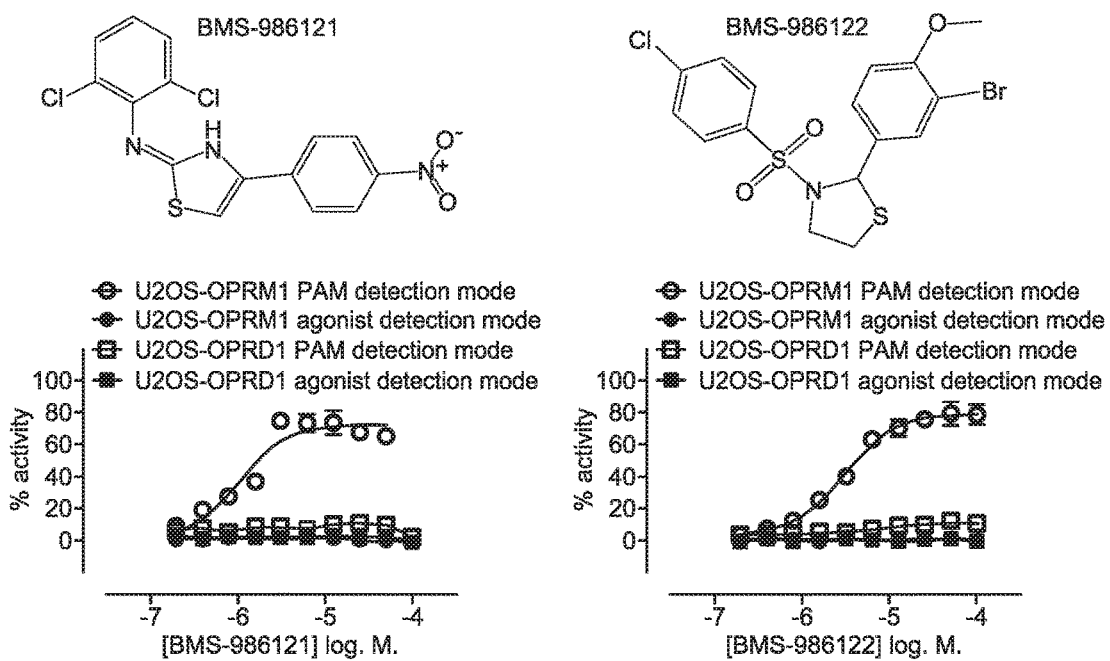
FIG. 1
Figure 2:
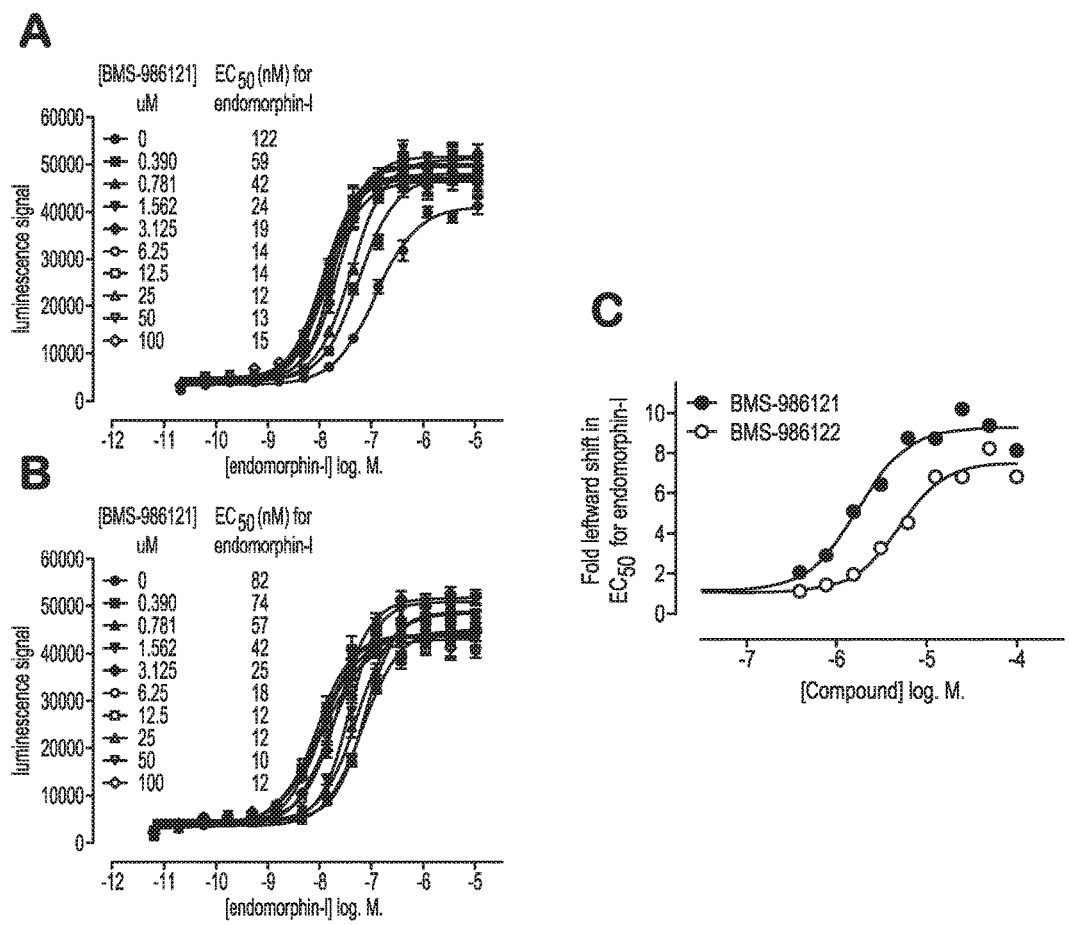
Figure 3:
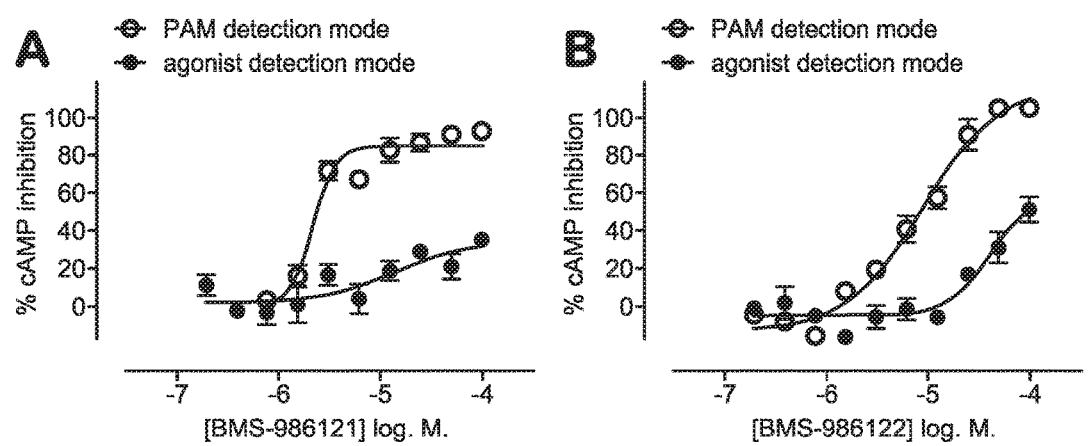
Figure 4:
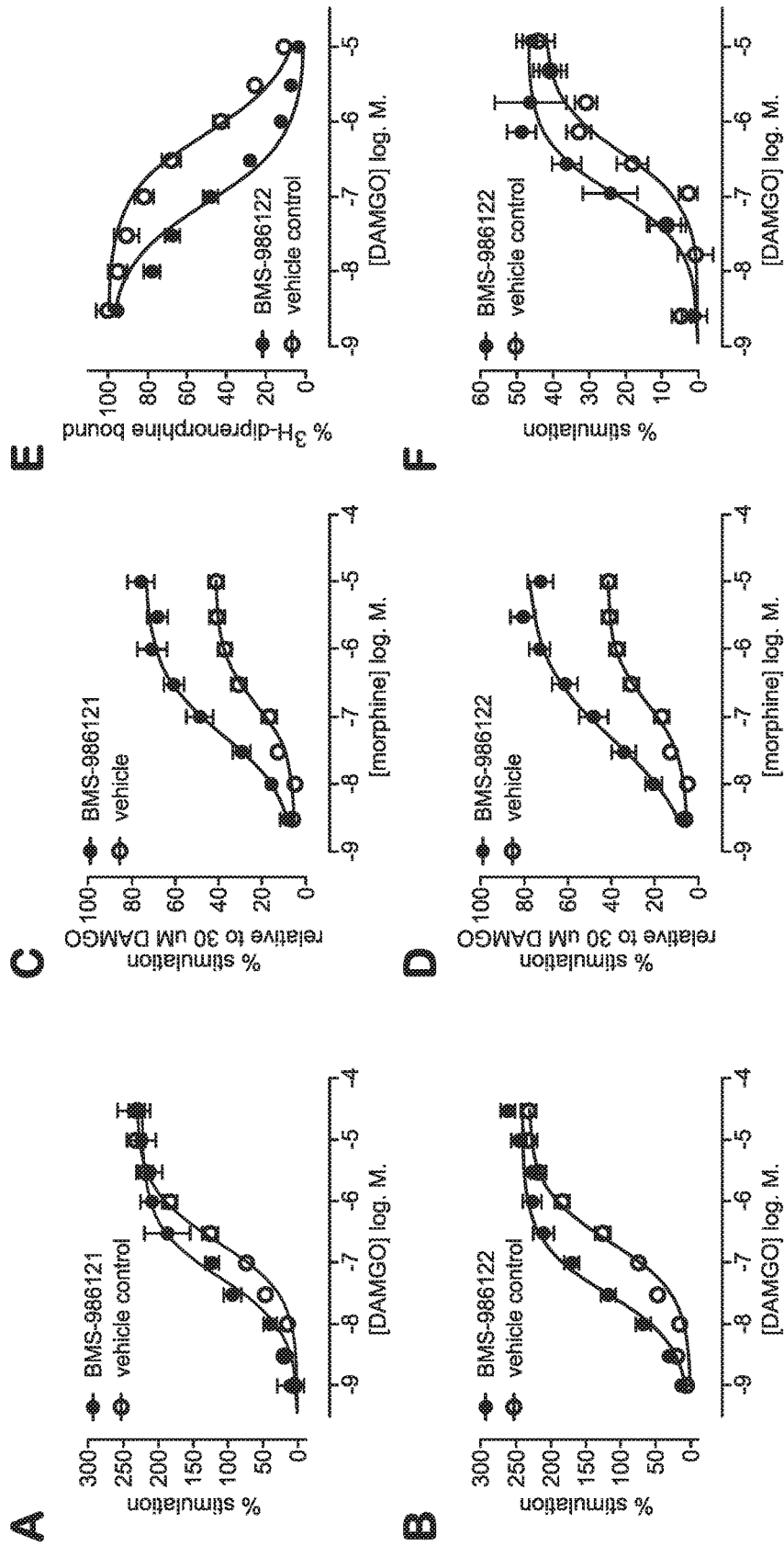
Figure 5:
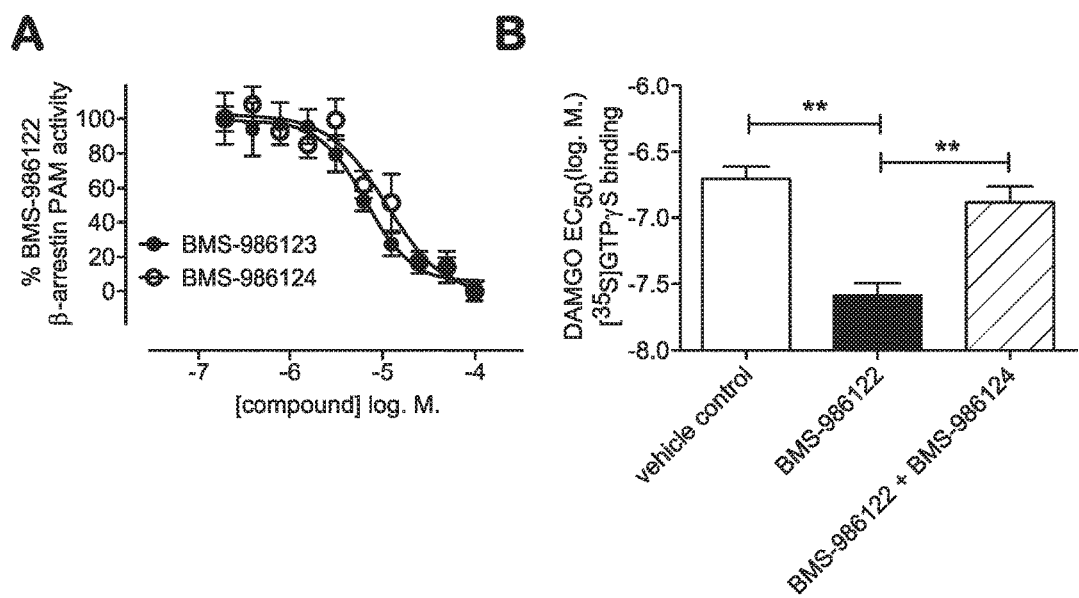
Figure 6:
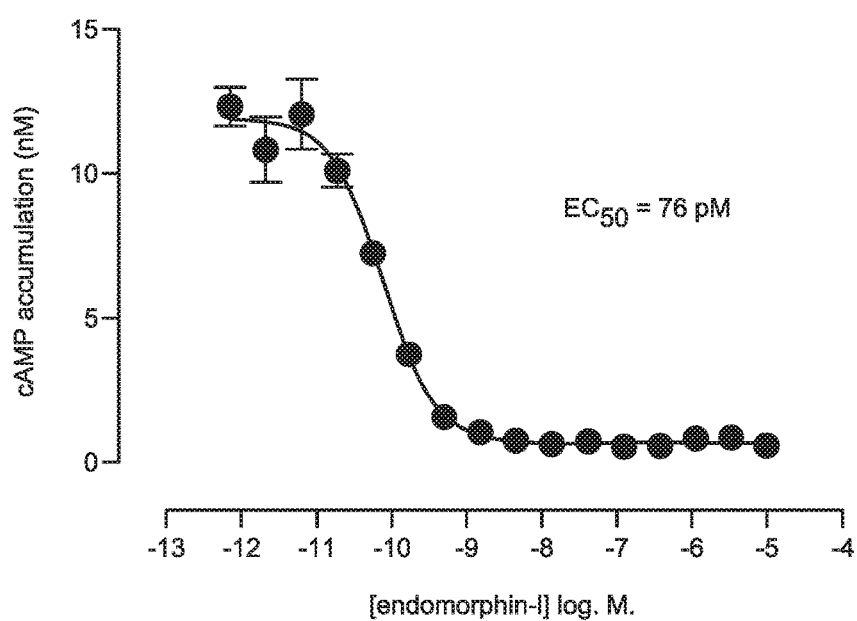

Effect of the mu-PAM, BMS-986122, and the SAM, BMS-986123, on [$^3$H]diprenorphine saturation binding in membranes from C6mu cells. BMS-986122 (A) had no significant effect on [$^3$H]diprenorphine binding affinity but induced a 6-fold increase in the affinity of DAMGO in competition binding studies (see FIG. 5, Compound C, Table S1). BMS-986123 (B) produced a small (~2-fold) but significant decrease in [$^3$H]diprenorphine affinity, but had no significant effect on DAMGO affinity (see Table S1). Data are represented as the mean ±s.e.m. of 3-7 experiments.

FIG. 8

Activity of BMS-986122 and 18 analogs in a β-arrestin recruitment assay in U2OS-OPRD1 and U2OS-OPRM1 cells. Compounds were tested in U2OS-OPRD1 cells in agonist detection mode (in the absence of leu-enkephalin) and PAM detection mode (in the presence of an ˜EC$_{10}$ concentration of leu-enkephalin). Compounds were also tested in U2OS-OPRM1 cells in agonist detection mode (in the absence of endomorphin-I) and PAM detection mode (in the presence of an ˜EC$_{10}$ concentration of endomorphin-I). Finally, compounds that exhibited no agonist or PAM activity in U2OS-OPRM1 cells were tested in SAM detection mode (in the presence of an ˜EC$_{20}$ concentration of endomorphin-I plus an ˜EC$_{80}$ of the PAM BMS-986122). Graphical curve fit data are representative of three combined experiments. EC$_{50}$ and E$_{max}$ values are represented in Table S2. For agonist detection mode, 0% and 100% activity represent basal activity and an Emax concentration of orthosteric agonist, respectively. For PAM detection mode, 0% activity represents the response to a low (˜EC$_{10}$) concentration of agonist alone, and 100% activity represents the response to an E$_{max}$ concentration of agonist. For SAM detection mode, 0% inhibition represents the response to a low (˜EC$_{20}$) concentration of endomorphin-I combined with an ˜EC$_{80}$ concentration of the mu-PAM BMS-986122. 100% inhibition represents the response to a low (˜EC$_{20}$) concentration of endomorphin-I alone.

FIG. 9

Effect of BMS-986123 and BMS-986124 on β-arrestin response to an ˜EC$_{80}$ concentration of endomorphin-I (antagonist/NAM detection mode) in U2OS-OPRM1 cells. BMS-986123 and BMS-986124 had no significant effect on endomorphin-I (300 nM) mediated β-arrestin activity in U2OS-OPRM1 cells. 100% activity is normalized to the response to endomorphin-I (300 nM) alone. 0% activity represents basal activity. Data are represented as the mean+s.e.m. of three experiments.

FIG. 10

Effect of BMS-986124 on BMS-986122-mediated PAM activity to DAMGO-stimulated [$^{35}$S]GTPγS binding in C6mu cell membranes. DAMGO-stimulated [$^{35}$S]GTPγS binding potency in C6mu membranes was increased 8-fold in the presence of the mu-PAM BMS-986122 (10 uM) (A). DAMGO-stimulated [$^{35}$S]GTPγS binding potency was not affected by incubation with 50 uM BMS-986124 (B). Co-incubation of BMS-986124 (50 uM) with BMS-986122 (10 uM) resulted in a rightward shift in DAMGO potency when compared to incubation with BMS-986122 alone (C). The potency of DAMGO, in the presence of both BMS-986122 and BMS-986124 was shifted leftward by only 2-fold compared with DAMGO potency in the presence of the vehicle control. These data suggest that BMS-986124 can antagonize the BMS-986122 PAM effect. Shown are the combined mean+s.e.m. data from 3-7 separate assays, each performed in duplicate. EC$_{50}$ values are given in the Results & Discussion section and in FIG. 5B.

FIG. 11

Effect of the SAMs BMS-986123 and BMS-986124 on DAMGO-stimulated [$^{35}$S]GTPγS binding above basal activity in membranes from C6mu cells. DAMGO potency (EC$_{50}$ of 222 (179-274) nM) was not significantly affected by BMS-986123 (A) (EC$_{50}$ of 321 239-432) nM) or BMS-986124 (B) (EC$_{50}$ of 223 (150-331) nM. The maximal stimulation by DAMGO (control max=232 (223-242) %, was not affected by BMS-986124 (243 (224-262) %. Maximal stimulation was decreased slightly by BMS-986123 (206 (193-218) %. The modulators did not significantly affect the basal values (vehicle control basal=3.2±0.2 fmol bound/mg protein). Shown are the combined data from 3-7 separate assays, each performed in duplicate.

FIG. 12

Effect of the SAMs BMS-986123 and BMS-986124 on morphine-stimulated [$^{35}$S]GTPγS binding in membranes from C6mu cells. The EC$_{50}$ of morphine to stimulate [$^{35}$S] GTPγS binding (110 (71-171) nM) was not significantly affected by BMS-986123 (A) (140 (67-293) nM; 67-293) nM), but was decreased by BMS-986124 (B) (245 (161-372) nM). The maximal effect of morphine compared to DAMGO (30 uM) (control max=42 (38-45) %) was increased to a small degree by BMS-986123 (62 (52-73) %) and BMS-986124 (58 (53-64) %). Shown are the combined data from 3-7 separate assays, each performed in duplicate.

FIG. 13

Effect of mu-PAM BMS-986121 on inhibition of forskolin-stimulated cAMP accumulation, mediated by different orthosteric agonists, in CHO-mu cells. BMS-986121 (100 uM) produced leftward shifts in agonist potency for each of the three orthosteric ligands used ((A) endomorphin-I=4-fold, (B) morphine=6.5-fold, and (C) leu-enkephalin=4.5-fold)). EC$_{50}$ values for the agonists at each BMS-986121 concentration are shown in the legend. Data represent the mean±s.e.m. of 3 experiments.

TABLE S1

Effect of the mu-PAM, BMS-986122, and the SAM, BMS-986123, on [$^3$H]diprenorphine saturation binding and DAMGO competition binding in membranes from C6mu cells.

| Compound added (10 uM) | [$^3$H]diprenorphine Kd (nM) mean (95% CI) | DAMGO Ki (nM) mean (95% CI) |
|---|---|---|
| Vehicle control | 0.27 (0.21-0.32) | 340 (208-552) |
| BMS-986122 | 0.35 (0.18-0.51) | 56 (41-76) |
| BMS-986123 | 0.71 (0.57-0.86) | 270 (179-406) |

TABLE S2

Structure activity relationship of BMS-986122 and analogs tested in the β-arrestin recruitment assay in U2OS-OPRM1 cells, in PAM detection mode. Compounds exhibiting PAM activity were described based on their efficacy as Full, Strong, Moderate, or Weak PAMs. 0% activity represents the response to a low (~$EC_{10}$) concentration of endomorphin-I alone and 100% activity represents the response to an $E_{max}$ concentration of endomorphin-I. The 2 compounds that showed no PAM activity were additionally tested in SAM detection mode (inhibition of BMS-986122 (~$EC_{80}$) response in the presence of a low concentration (~$EC_{20}$) of endomorphin-I) where the compounds were shown to inhibit the BMS-986122 response (FIG. S3). Calculated $K_b$ values are provided from $IC_{50}$ values. Concentration response curves for the SAM compounds, BMS-986123 and BMS-986124, are shown in FIG. 5A. Data are represented as the mean of 3 experiments.

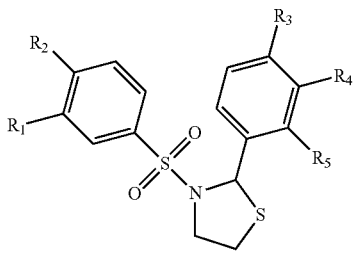

| Substance | R1 | R2 | R3 | R4 | R5 | β-arrestin PAM Detection Mode (% $E_{min}$) | β-arrestin PAM detection mode ($EC_{max}$ uM) | Description | β-arrestin SAM Detection Mode ($K_b$, uM) |
|---|---|---|---|---|---|---|---|---|---|
| BMS-986122 | H | Cl | OMe | Br | H | 79 | 3 | Full PAM (ref) | |
| Analog 1 | H | Nitro | OMe | Br | H | 53 | 2 | Moderate PAM | |
| Analog 2 | H | Me | OMe | Br | H | 18 | 4 | Weak PAM | |
| Analog 3 | H | OMe | OMe | Br | H | 16 | 6 | Weak PAM | |
| Analog 4 | Me | H | OMe | Br | H | 20 | 9 | Weak PAM | |
| Analog 5 | H | Cl | OMe | Nitro | H | 45 | 4 | Moderate PAM | |
| Analog 6 | H | Br | OMe | Nitro | H | 45 | 2 | Moderate PAM | |
| Analog 7 (BMS-986123) | H | Me | OMe | Nitro | H | — | — | SAM | 1 |
| Analog 8 | H | Br | OMe | OMe | H | 18 | 14 | Weak PAM | |
| Analog 9 | H | Br | OMe | H | H | 44 | 7 | Moderate PAM | |
| Analog 10 | H | H | OMe | H | H | 17 | 23 | Weak PAM | |
| Analog 11 | H | Cl | H | Cl | H | 65 | 5 | Strong PAM | |
| Analog 12 | H | Cl | Br | H | H | 26 | 6 | Weak PAM | |
| Analog 13 (BMS-986124) | H | Cl | Br | H | OMe | — | — | SAM | 2 |
| Analog 14 | H | OMe | Br | H | H | 3 | 7 | Weak PAM | |
| Analog 15 | H | OMe | OMe | H | H | 9 | 37 | Weak PAM | |

BIBLIOGRAPHY

1. Jacoby, E., Bouhelal, R., Gerspacher, M., & Seuwen, K. (2006) The 7 TM G-protein-coupled receptor target family. *ChemMedChem* 1: 761-782.
2. Overington, J. P., Al-Lazikani, B., & Hopkins, A. L. (2006) How many drug targets are there? *Nature reviews* 5: 993-996.
3. Waldhoer, M., Bartlett, S. E., & Whistler, J. L. (2004) Opioid receptors. *Annual review of biochemistry* 73: 953-990.
4. Whalen, E. J., Rajagopal, S., & Lefkowitz, R. J. (2011) Therapeutic potential of beta-arrestin- and G protein-biased agonists. *Trends in molecular medicine* 17: 126-139.
5. Shukla, A. K., Xiao, K., & Lefkowitz, R. J. (2011) Emerging paradigms of beta-arrestin-dependent seven transmembrane receptor signaling. *Trends in biochemical sciences* 36: 457-469.
6. Matthes, H. W., Maldonado, R., Simonin, F., Valverde, O., Slowe, S., Kitchen, I., Befort, K., Dierich, A., Le Meur, M., Dolle, P., et al. (1996) Loss of morphine-induced analgesia, reward effect and withdrawal symptoms in mice lacking the mu-opioid-receptor gene. *Nature* 383: 819-823.
7. Manglik, A., Kruse, A. C., Kobilka, T. S., Thian, F. S., Mathiesen, J. M., Sunahara, R. K., Pardo, L., Weis, W. I., Kobilka, B. K., & Granier, S. (2012) Crystal structure of the micro-opioid receptor bound to a morphinan antagonist. *Nature* 485: 321-326.
8. McNicol, E., Horowicz-Mehler, N., Fisk, R. A., Bennett, K., Gialeli-Goudas, M., Chew, P. W., Lau, J., & Carr, D.

(2003) Management of opioid side effects in cancer-related and chronic noncancer pain: a systematic review. *J Pain* 4: 231-256.
9. Davis, M. P. (2012) Evidence from basic research for opioid combinations. *Expert opinion on drug discovery* 7: 165-178.
10. Dietis, N., Guerrini, R., Calo, G., Salvadori, S., Rowbotham, D. J., & Lambert, D. G. (2009) Simultaneous targeting of multiple opioid receptors: a strategy to improve side-effect profile. *British journal of anaesthesia* 103: 38-49.
11. Burford, N. T., Watson, J., Bertekap, R., & Alt, A. (2011) Strategies for the identification of allosteric modulators of G-protein-coupled receptors. *Biochemical pharmacology* 81: 691-702.
12. Kenakin, T. P. (2009) '7TM receptor allostery: putting numbers to shapeshifting proteins. *Trends Pharmacol Sci* 30: 460-469.
13. Birdsall, N. J. & Lazareno, S. (2005) Allosterism at muscarinic receptors: ligands and mechanisms. *Mini reviews in medicinal chemistry* 5: 523-543.
14. Bruns, R. F. & Fergus, J. H. (1990) Allosteric enhancement of adenosine A1 receptor binding and function by 2-amino-3-benzoylthiophenes. *Molecular pharmacology* 38: 939-949.
15. Conn, P. J., Jones, C. K., & Lindsley, C. W. (2009) Subtype-selective allosteric modulators of muscarinic receptors for the treatment of CNS disorders. *Trends in Pharmacological Sciences* 30: 148-155.
16. Gao, Z. G., Kim, S. K., Ijzerman, A. P., & Jacobson, K. A. (2005) Allosteric modulation of the adenosine family of receptors. *Mini reviews in medicinal chemistry* 5: 545-553.
17. Gasparini, F., Kuhn, R., & Pin, J. P. (2002) Allosteric modulators of group I metabotropic glutamate receptors: novel subtype-selective ligands and therapeutic perspectives. *Current opinion in pharmacology* 2: 43-49.
18. Bassoni, D. L., Raab, W. J., Achacoso, P. L., Loh, C. Y., & Wehrman, T. S. (2012) Measurements of beta-arrestin recruitment to activated seven transmembrane receptors using enzyme complementation. *Methods in molecular biology* (Clifton, N.J 897: 181-203.
19. Clark, M. J., Furman, C. A., Gilson, T. D., & Traynor, J. R. (2006) Comparison of the relative efficacy and potency of mu-opioid agonists to activate Galpha(i/o) proteins containing a pertussis toxin-insensitive mutation. *The Journal of pharmacology and experimental therapeutics* 317: 858-864.
20. Noetzel, M. J., Rook, J. M., Vinson, P. N., Cho, H. P., Days, E., Zhou, Y., Rodriguez, A. L., Lavreysen, H., Stauffer, S. R., Niswender, C. M., et al. (2012) Functional impact of allosteric agonist activity of selective positive allosteric modulators of metabotropic glutamate receptor subtype 5 in regulating central nervous system function. *Molecular pharmacology* 81: 120-133.
21. Langmead, C. J. (2012) Ligand properties and behaviours in an allosteric age. *Trends Pharmacol Sci* 33: 621-622.
22. Alt, A., Mansour, A., Akil, H., Medzihradsky, F., Traynor, J. R., & Woods, J. H. (1998) Stimulation of guanosine-5'-O-(3-[35S]thio)triphosphate binding by endogenous opioids acting at a cloned mu receptor. *The Journal of pharmacology and experimental therapeutics* 286: 282-288.
23. Sharma, S., Rodriguez, A. L., Conn, P. J., & Lindsley, C. W. (2008) Synthesis and SAR of a mGluR5 allosteric partial antagonist lead: Unexpected modulation of pharmacology with slight structural modifications to a 5-(phenylethynyl)pyrimidine scaffold. *Bioorganic & Medicinal Chemistry Letters* 18: 4098-4101.
24. Koole, C., Wootten, D., Simms, J., Valant, C., Sridhar, R., Woodman, O. L., Miller, L. J., Summers, R. J., Christopoulos, A., & Sexton, P. M. (2010) Allosteric ligands of the glucagon-like peptide 1 receptor (GLP-1R) differentially modulate endogenous and exogenous peptide responses in a pathway-selective manner: implications for drug screening. *Molecular pharmacology* 78: 456-465.
25. Rogues, B. P., Fournie-Zaluski, M. C., & Wurm, M. (2012) Inhibiting the breakdown of endogenous opioids and cannabinoids to alleviate pain. *Nature reviews* 11: 292-310.
26. Levine, J. D., Gordon, N. C., Jones, R. T., & Fields, H. L. (1978) The narcotic antagonist naloxone enhances clinical pain. *Nature* 272: 826-827.
27. Gjoni, T. & Urwyler, S. (2008) Receptor activation involving positive allosteric modulation, unlike full agonism, does not result in GABAB receptor desensitization. *Neuropharmacology* 55: 1293-1299.
28. Davis, C. N., Bradley, S. R., Schiffer, H. H., Friberg, M., Koch, K., Tolf, B. R., Bonhaus, D. W., & Lameh, J. (2009) Differential regulation of muscarinic M1 receptors by orthosteric and allosteric ligands. *BMC pharmacology* 9: 14.
29. Emmerson, P. J., Clark, M. J., Mansour, A., Akil, H., Woods, J. H., & Medzihradsky, F. (1996) Characterization of opioid agonist efficacy in a C6 glioma cell line expressing the mu opioid receptor. *The Journal of pharmacology and experimental therapeutics* 278: 1121-1127.
30. Clark, M. J., Harrison, C., Zhong, H., Neubig, R. R., & Traynor, J. R. (2003) Endogenous RGS protein action modulates mu-opioid signaling through Galphao. Effects on adenylyl cyclase, extracellular signal-regulated kinases, and intracellular calcium pathways. *The Journal of biological chemistry* 278: 9418-9425.
31. Lester, P. A. & Traynor, J. R. (2006) Comparison of the in vitro efficacy of mu, delta, kappa and ORL1 receptor agonists and non-selective opioid agonists in dog brain membranes. *Brain research* 1073-1074: 290-296.
32. Bradford, M. M. (1976) A rapid and sensitive method for the quantitation of microgram quantities of protein utilizing the principle of protein-dye binding. *Analytical biochemistry* 72: 248-254.
33. Neilan, C. L., Akil, H., Woods, J. H., & Traynor, J. R. (1999) Constitutive activity of the delta-opioid receptor expressed in C6 glioma cells: identification of non-peptide delta-inverse agonists. *British journal of pharmacology* 128: 556-562.
34. Lee, K. O., Akil, H., Woods, J. H., & Traynor, J. R. (1999) Differential binding properties of oripavines at cloned mu- and delta-opioid receptors. *European journal of pharmacology* 378: 323-330.

The invention claimed is:
1. A method of treating pain in a patient in need thereof comprising administering to the patient a compound which is a positive allosteric modulator for the mu-opioid receptor wherein the compound is selected from the group consisting of

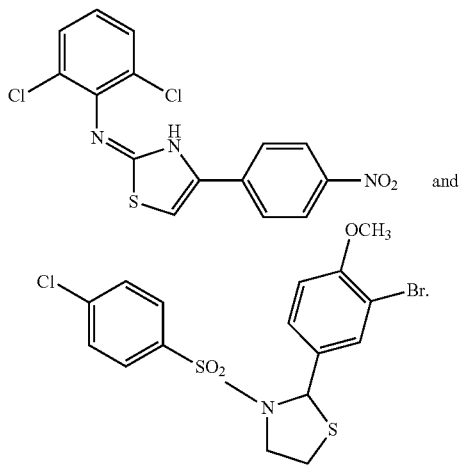

2. The method of claim 1, further comprising administering an orthosteric agonist for the mu-opioid receptor.

3. A method of modulating the mu-opioid receptor comprising contacting the receptor with a compound that is effective to provide an increase in the receptor function in the presence of orthosteric exogenous or endogenous agonist wherein the compound is selected from the group consisting of

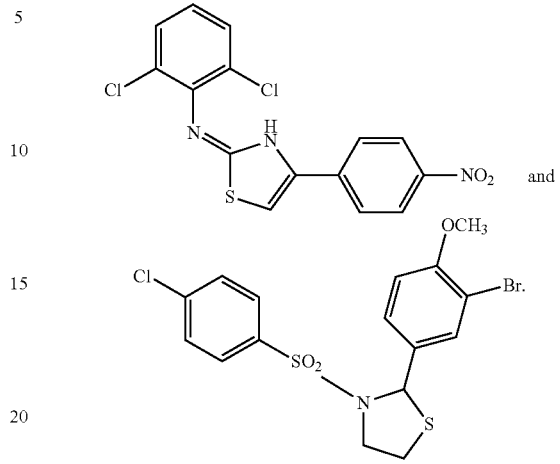

4. The method of claim 3 wherein the increase in receptor function is observed in maximal effect, potency, or both.

* * * * *